US011498974B2

(12) United States Patent
Lannfelt et al.

(10) Patent No.: US 11,498,974 B2
(45) Date of Patent: Nov. 15, 2022

(54) BRAIN DELIVERY PROTEIN

(71) Applicant: BioArctic AB, Stockholm (SE)

(72) Inventors: Lars Lannfelt, Stockholm (SE); Dag Sehlin, Uppsala (SE); Greta Hultqvist, Uppsala (SE); Stina Syvänen, Uppsala (SE)

(73) Assignee: BioArctic AB, Stockholm (SE)

( * ) Notice: Subject to any disclaimer, the term of this patent is extended or adjusted under 35 U.S.C. 154(b) by 0 days.

(21) Appl. No.: 16/317,156

(22) PCT Filed: Jul. 13, 2017

(86) PCT No.: PCT/EP2017/067727
§ 371 (c)(1),
(2) Date: Jan. 11, 2019

(87) PCT Pub. No.: WO2018/011353
PCT Pub. Date: Jan. 18, 2018

(65) Prior Publication Data
US 2019/0225699 A1 Jul. 25, 2019

(30) Foreign Application Priority Data

Jul. 14, 2016 (SE) .................................. 1651065-3

(51) Int. Cl.
C07K 16/28 (2006.01)
C07K 16/18 (2006.01)
A61K 47/54 (2017.01)
A61K 47/68 (2017.01)
A61P 25/28 (2006.01)
A61P 25/18 (2006.01)
A61P 25/16 (2006.01)
G01N 33/68 (2006.01)
A61K 39/00 (2006.01)

(52) U.S. Cl.
CPC ........ C07K 16/2881 (2013.01); A61K 47/555 (2017.08); A61K 47/6801 (2017.08); A61P 25/16 (2018.01); A61P 25/18 (2018.01); A61P 25/28 (2018.01); C07K 16/18 (2013.01); G01N 33/6896 (2013.01); A61K 2039/505 (2013.01); C07K 2317/31 (2013.01); C07K 2317/622 (2013.01)

(58) Field of Classification Search
None
See application file for complete search history.

(56) References Cited

U.S. PATENT DOCUMENTS

2008/0152645 A1* 6/2008 Pardridge ............ A61P 31/00
424/130.1
2009/0270465 A1 10/2009 Albright et al.
2011/0135644 A1 6/2011 Hulmann-Cottier et al.
2015/0056134 A1* 2/2015 Sawada ............ A61K 51/1057
424/1.49

FOREIGN PATENT DOCUMENTS

| EA | 021758 B1 | 8/2015 |
| RU | 2522245 C2 | 7/2014 |
| WO | 2007/108756 A1 | 9/2007 |
| WO | 2011/160083 A1 | 12/2011 |
| WO | 2012/075037 A1 | 6/2012 |
| WO | 2014/033074 A1 | 3/2014 |
| WO | 2015/155694 A1 | 10/2015 |
| WO | 2016/005466 A2 | 1/2016 |

OTHER PUBLICATIONS

Reitz "Toward precision medicine in Alzheimer's disease" Ann Transl Med 2016;4(6):107 (Year: 2016).*
Stanford "Alzheimer's Prevention, Treatment and Research—A Q&A with Dr. Frank Longo" accessed from stanfordhealthcare.org (Year: 2016).*
Dictionary "prophylaxis" accessed from dictionary.com (Year: 2021).*
Mayo "Diagnostic tests for newborns" accessed from mayoclinic.org (Year: 2021).*
Lennox "Intravenous immunoglobulin and rituximab versus placebo treatment of antibodyassociated psychosis: study protocol of a randomised phase IIa double-blinded placebo-controlled trial (SINAPPS2)" Lennox et al. Trials (2019) 20:331 (Year: 2019).*
Bard, Frédérique et al., Peripherally administered antibodies against amyloid β-peptide enter the central nervous system and reduce pathology in a mouse model of Alzheimer disease, Nature Medicine, vol. 6, No. 8, pp. 916-919 (Aug. 2000).
Boado, Ruben et al., Engineering and Expression of a Chimeric Transferrin Receptor Monoclonal Antibody for Blood-Brain Barrier Delivery in the Mouse, Biotechnol Bioeng., vol. 102, No. 4, pp. 1251-1258 (Mar. 1, 2009).
Yu, Joy Y. et al., Developing Therapeutic Antibodies for Neurodegenerative Disease, Neurotherapeutics, vol. 10, pp. 459-472 (2013).
Niewoehner, Jens et al., Increased Brain Penetration and Potency of a Therapeutic Antibody Using a Monovalent Molecular Shuttle, Neuron, vol. 81, pp. 49-60 (Jan. 8, 2014).
Pardridge, William M., Blood—brain barrier drug delivery of IgG fusion proteins with a transferrin receptor monoclonal antibody, Expert Opin. Drug Deliv., vol. 12, No. 2, pp. 207-222 (2015).

(Continued)

Primary Examiner — Adam Weidner

(74) Attorney, Agent, or Firm — Marshall, Gerstein & Borun LLP

(57) ABSTRACT

The present invention relates to a brain delivery protein, comprising a target binding antibody which binds to a target in a mammalian brain; two carrier moieties, each of which being capable of monovalent interaction with a protein expressed on a blood brain barrier (BBB) endothelial cell, wherein each of said carrier moieties is linked to a C-terminal end of the target binding antibody. The present invention moreover relates to use of such brain delivery proteins in therapy or diagnosis or for research of e.g. neurodegenerative disorders, and other brain diseases.

27 Claims, 10 Drawing Sheets
Specification includes a Sequence Listing.

(56) References Cited

OTHER PUBLICATIONS

Sade, Hadassah et al., A Human Blood-Brain Barrier Transcytosis Assay Reveals Antibody Transcytosis Influenced by pH-Dependent Receptor Binding, PLOS ONE, vol. 9, No. 4, pp. 1-11 (Apr. 2014).
Sehlin, Dag et al., Antibody-based PET imaging of amyloid beta in mouse models of Alzheimer's disease, Nature Communications, vol. 7:10759, pp. 1-11 (2016).
Yu, Joy Y. et al., Boosting Brain Uptake of a Therapeutic Antibody by Reducing Its Affinity for a Transcytosis Target, vww.ScienceTranslationalMedicine.org, vol. 3, Issue 84, pp. 1-9 (May 25, 2011).

* cited by examiner

BRAIN DELIVERY PROTEIN

The Sequence Listing submitted herewith, entitled "Jan-11-2019-SEQ-LIST_ST25.TXT", created Nov. 16, 2018, and having a size of 626 bytes, is incorporated herein by reference.

TECHNICAL FIELD

The present invention relates to a brain delivery protein, which enables transportation of a protein, such as an antibody, which binds to a target in the brain, across the blood brain barrier.

BACKGROUND

The blood brain barrier (BBB) is comprised of tightly connected endothelial cells and serves as a protector of the brain by keeping both small drug-like molecules and larger molecules like proteins outside the brain. Although essential for brain homeostasis, the presence of this barrier is an obstacle to treatment and diagnostics of diseases in the brain. For example, only around 0.1% of unmodified antibodies enter the brain due to the tightly connected endothelial cells of the BBB (Bard F. et al, Nat. Med. 6: 916-919 (2000)).

However, active transport from blood across the BBB into the brain has been described for some proteins. One such example is transferrin that transports iron to the brain via the transferrin receptor (TfR) located at the BBB. The transferrin-TfR complex is formed at the luminal side of the BBB and subsequently endocytosed. Iron dissociates from the transferrin in the endosomes where the pH is lower. Transferrin with no iron bound, apotransferrin, has a low affinity for the TfR and is released together with the iron at the abluminal side of the BBB. Not only transferrin but also other proteins that bind to the TfR can be endocytosed from the luminal to the abluminal side of the BBB and this mechanism can be exploited to actively transport molecules into the brain (Boado R J. et al, Biotechnol. Bioeng. 102: 1251-1258 (2009); Pardridge W M, Expert Opin. Drug Deliv. 12: 207-222 (2015)).

To avoid degradation in the lysosomes, it is necessary that the protein/antibody binding to the TfR dissociates from the receptor in the endosome. It has been proposed that the dissociation from TfR can be facilitated by the low pH environment in the endosome for binders that display pH dependent affinity (Sade H. et al, PLOS one 4: e96340 (2014)). Dissociation is also more likely when the overall affinity to TfR is moderate or low (Yu Y J. et al, Sci. Transl. Med. 3: 84ra44 (2011)). Bivalent binding to the target has also been found to be disadvantageous (Niewoehner J. et al, Neuron 81: 49-60 (2014)). Antibody bivalent binding decreases the rate of dissociation from the TfR since antibody dissociation requires a simultaneous dissociation from two epitopes (binding sites) i.e. the avidity effect A bispecific protein consisting of an anti-amyloid β protofibril antibody, referred to as mAb158, chemically conjugated to a TfR antibody 8D3 has previously been disclosed (Sehlin D. et al, Nat. Commun. 7: 10759 (2016)). This protein displayed 20-fold higher brain-to-blood concentrations than mAb158 at 3 days post injection. The increased ratio was found to be partly due to increased brain concentration and partly due to a decreased half-life in blood compared with mAb158.

An antibody with low affinity to a BBB receptor has previously been disclosed in WO 2012/075037. Moreover, this publication discloses differences observed in brain uptake for a bispecific antibody (anti-TfR$^A$/BACE1) that binds both TfR and the amyloid precursor protein (APP) cleavage enzyme, beta secretase (BACE1), between administration at a trace dose and at a therapeutic dose.

In WO 2014/033074 another variant of a BBB antibody shuttle is disclosed. The BBB shuttle comprises a brain effector entity, a linker and one monovalent binding entity which binds to TfR, wherein the linker couples the effector entity to the monovalent binding entity which binds to the TfR.

In order to provide improved therapy and diagnosis of diseases in the brain, and for research purposes, there is still need for proteins/antibodies with improved uptake.

SUMMARY OF THE INVENTION

It is an object of the present invention to provide novel proteins for treatment and diagnosis of diseases in the brain, as well as for research purposes.

There is, in a first aspect of the invention, provided a brain delivery protein, comprising
  a target binding antibody or fragment thereof which binds to a target in a mammalian brain;
  two carrier moieties, each of which being capable of monovalent interaction with a protein expressed on a blood brain barrier (BBB) endothelial cell,
  wherein each of said carrier moieties is linked to a C-terminal end of the target binding antibody.

The brain delivery protein as disclosed herein comprises two types of moieties; a target binding antibody which binds to a target in the brain and two carrier moieties which enable transportation of the brain delivery protein across the BBB into the brain. Both carrier moieties are capable of monovalent interaction with, or monovalent binding to, a protein on a BBB endothelial cell. Monovalent interaction or binding indicates that the interaction between the carrier moiety and the protein expressed on a BBB endothelial cell takes place through one single epitope. Due to the structure of the brain delivery protein, typically only one of the carrier moieties at a time may bind to the protein expressed on the BBB. This may in turn prevent bivalent, high avidity binding to the BBB protein and lead to a more efficient BBB transfer, and may also prevent any dimerization/conformational change of the BBB protein.

In one embodiment, one of said two carrier moieties binds at a time to said protein expressed on a BBB endothelial cell. Monovalent interaction of the brain delivery protein as such with the protein expressed on the BBB endothelial cell is thus enabled.

Thus, by maintaining monovalent binding despite having two carrier moieties that potentially may bind to said BBB protein, the efficiency of transport across the BBB may be increased. By having two carrier moieties connected to the target binding antibody, the number of available binding sites to a protein expressed on BBB cells will be doubled compared to a brain delivery protein comprising only one carrier moiety. Dosing experiments conducted in mice moreover demonstrated that a brain delivery protein according to the present invention comprising two carrier moieties improves brain uptake at both therapeutic and trace doses (Example 2). The specific brain delivery protein studied in Example 2, RmAb158-scFv8D3, with two single chain TfR binding antibodies (scFv8D3), was found to increase brain uptake by approximately 80 times at 2 h post injection at trace dosing, compared to the brain uptake of a "naked" target binding antibody (RmAb158) without carrier moiety. Similar results have been obtained for RmAb48-scFv8D3 (Example 5). At therapeutic dosing the brain uptake of RmAb158-scFv8D3 was found to be 10 times higher than the brain uptake of the corresponding naked target binding antibody. It is hypothesized that this difference may, at least in part, depend on the brain delivery protein having two TfR binding moieties. By comparison, brain shuttles of the prior art have demonstrated approximately 40 times increased uptake of anti-TfR antibody at trace dosing, whereas brain uptake of the same shuttle at therapeutic doses is increased only 1.4 times (Yu et al, supra, (2011)). This might be due to the TfR system getting saturated at therapeutic doses. Similar results have however been previously published for a brain shuttle based on CD98 as a BBB shuttle. At trace dosing the uptake was found to be 80 times higher than antibody without CD98 but at therapeutic dosing it was only 3.2 times higher (Zuchero Y J Y. et al, Neuron 89: 70-82 (2016)).

The carrier moieties of the brain delivery protein as disclosed herein are linked to the target binding antibody at a C-terminal end of the target binding antibody. The carrier moieties are preferably located at a C-terminal end of a heavy chain or at a light chain of the target binding antibody. Preferably, the carrier moieties are linked to separate chains of the target binding antibody, preferably to a separate light chain or to a separate heavy chain.

According to one embodiment, each of said carrier moieties is linked to the target binding antibody by a linker. The linkers for connecting the carrier moieties to the target binding antibody may be the same or different, i.e. they may have identical length and/or amino acid sequences, or they may have different length and/or amino acid sequences. In particular, in respect of each of said carrier moieties, each of said linkers individually comprises a peptide having an amino acid sequence consisting of 1-30 amino acid residues, preferably 1-25 amino acid residues, preferably 1-19 amino acid residues, preferably 3-19 amino acid residues, preferably 3-15 amino acid residues, preferably 5-15 amino acid residues. One example of a linker is a linker having 11 amino acids. Such a linker length has been used in the appended examples. Thus, said linker is preferably a relatively short peptide. However, the length of the linker may be different depending on the specific position of the linker on the target binding antibody. A short linker may be advantageous in that the carrier moieties may be further sterically hindered to bivalently bind to a protein, e.g. a dimeric receptor, expressed on an endothelial BBB cell. Compared with bivalent binding, monovalent binding with a protein expressed on a BBB endothelial cell might provide improved transfer across the BBB. Bivalent binding decreases the rate of dissociation, which in turn may increase the probability of binding and hence the binding time, i.e. the avidity effect leading to reduced BBB transport.

In one embodiment, each of said two carrier moieties is linked to a C-terminal end of a light chain of the target binding antibody. In particular, a brain delivery protein comprising two carrier moieties linked to said target binding antibody by short peptide linkers, e.g. each linker comprising a peptide having 1-30 amino acid residues, may still enable monovalent interaction with the protein expressed on BBB endothelial cells. For example, each linker may comprise a peptide having 1-25 amino acids, preferably 1-19 amino acids, more preferably 5-19 amino acids. A non-limiting example of a linker for linking each of the carrier moieties to the C-terminal ends of the light chains of the target binding antibody is a linker having a length of 11 amino acid residues. Such a linker is disclosed in the appended examples. It should be understood that the linkers for linking the carrier moieties with the target binding antibody could be identical or different, i.e. they may have identical length and/or amino acid sequences, or they may have different length and/or amino acid sequences.

In one embodiment, each of said two carrier moieties is linked to a C-terminal end of a heavy chain of the target binding antibody. In particular, a brain delivery protein comprising two carrier moieties linked to said target binding antibody by short peptide linkers, e.g. each linker comprising a peptide having 1-19 amino acid residues, may still enable monovalent interaction with the protein expressed on BBB endothelial cells. For example, each linker may comprise a peptide having 1-19 amino acids, preferably 1-15 amino acids, more preferably 1-10 amino acids. It should be understood that the linkers linking the carrier moieties with the target binding antibody could be identical or different, i.e. they may have identical length and/or amino acid sequences, or they may have different length and/or amino acid sequences.

In one embodiment, a first carrier moiety is linked to a C-terminal of a heavy chain of the target binding antibody, and a second carrier moiety is linked to a C-terminal end of a light chain of the target binding antibody. It should be understood that the linkers linking the carrier moieties with the target binding antibody could be identical or different, i.e. they may have identical length and/or amino acid sequences, or they may have different length and/or amino acid sequences. Example lengths of linkers are disclosed in related embodiments herein.

As disclosed in the appended examples, a relatively short peptide linker, linking two carrier moieties (scFv8D3) to the C-terminal ends of the light chain of a target binding antibody (RmAb158), has been found to sterically hinder bivalent binding to the protein expressed on the BBB (TfR dimer). The peptide linker used in the appended examples was flexible and hydrophilic, and contained 11 amino acid residues. Thus, one non-limiting example of a linker that may be used in the brain delivery protein according to the present invention is a linker comprising a peptide having the amino acid sequence APGSYTGSAPG (SEQ ID NO:1). Peptide linkers having different lengths and amino acid sequences are also encompassed by the present disclosure. The skilled person would understand how to design alternative linker sequences, i.e. select alternative amino acid residues having/providing similar properties in terms of e.g. hydrophilicity and flexibility.

In one embodiment, said linker is flexible. A flexible linker may comprise amino acid residues having small side chains. A non-limiting example of a flexible peptide linker is a glycine rich linker. In one embodiment, said linker is hydrophilic. Thus, a hydrophilic linker typically comprises hydrophilic amino acid residues. In one embodiment, said linker comprises a peptide comprising at least one proline residue, such as two proline residues. Such a proline residue(s) is/are preferably located near the C- and/or N-terminal ends of the linker sequence.

The term "antibody" is used herein in its broadest sense, including both monoclonal and polyclonal antibodies, and full-length antibodies such as full length IgG and other antibody isotypes and subtypes. A full-length antibody should be understood as an antibody comprising an antigen-binding variable region as well as a light chain constant domain (CL) and heavy chain constant domains, CH1, CH2 and CH3. Included in the term "antibody" is also antibody fragments such as Fab, Fab', F(ab')$_2$ and Fv fragments. Single chain fragments thereof such as scFv, Fv, sFab, V$_{HH}$ or a VNAR are also encompassed by the term as used herein. Thus, in one embodiment the target binding antibody is selected from an antibody and a fragment thereof as mentioned above. Antibodies as referred to herein are preferably humanized antibodies.

In one embodiment, each of said carrier moieties comprises an antibody or an antibody fragment. Said antibody fragment may be selected from a scFv, Fv, scFab, or a V$_{HH}$; transferrin or a mutant or variant thereof, or a variant of protein Z derived from domain B of staphylococcal protein A. Said antibody or an antibody fragment is preferably humanized.

In one embodiment, each of said carrier moieties comprises a scFv. By using single chain fragments of an antibody, manufacturing of the brain delivery protein may for example be simplified.

It should be understood that several different proteins expressed on BBB endothelial cells could be exploited as transportation pathways into the brain for a target binding antibody. Such transportation pathways may utilize receptor-mediated transcytosis for delivery of e.g. antibodies across the BBB. Thus, in one embodiment, said protein expressed on a BBB endothelial cell is selected from transferrin receptor (TfR), insulin receptor (InsR), insulin-like growth factor receptor, low density lipoprotein receptor-related protein 8 (Lrp8), low density lipoprotein receptor-related protein 1 (Lrp1), CD98, transmembrane protein 50A (TMEM50A), glucose transporter 1 (Glut1), basigin (BSG) and heparin-binding epidermal growth factor-like growth factor. Preferably, said protein expressed on a BBB endothelial cell is selected from TfR, InsR, Lrp1, CD98, Glut1 and BSG. In one embodiment, said protein expressed on a BBB endothelial cell is TfR. In one embodiment, said protein expressed on a BBB endothelial cell is InsR. In one embodiment, said protein expressed on a BBB endothelial cell is Lrp1. In one embodiment, said protein expressed on a BBB endothelial cell is CD98. In one embodiment, said protein expressed on a BBB endothelial cell is Glut1. In one embodiment, said protein expressed on a BBB endothelial cell is BSG.

It should thus be understood that said two carrier moieties each are capable of monovalent interaction with a protein expressed on a BBB endothelial cell, as exemplified above. In particular, each of said carrier moieties may be an antibody or a protein capable of interacting with for example TfR, InsR, Lrp1, CD98, Glut1 or BSG. In one embodiment, each of said carrier moieties is an antibody fragment directed to TfR. An example of an anti-TfR binding antibody is 8D3. A single chain fragment of the variable domain (scFv8D3) has, as demonstrated in the appended examples, proven advantageous in an example of a brain delivery protein according to the invention.

In one embodiment, each of said carrier moieties is an anti-TfR antibody which has low-to-moderate affinity for TfR. An anti-TfR carrier antibody having low-to-moderate affinity for TfR may, compared to a high affinity counterpart, improve brain uptake and distribution of the brain delivery protein, since the TfR system first of all seemingly is saturated at therapeutic doses. Whereas a high affinity variant of an anti-TfR antibody at therapeutic dosing may saturate the TfR system, a low or moderate affinity anti-TfR variant antibody may at the same dosing avoid such TfR saturation. In addition, a low or moderate affinity variant may, compared to a high affinity variant, be released more quickly after encapsulation in the endosome. The high affinity variant may not be released at all which may thus result in degradation of the protein. Moreover, antibodies with less affinity for TfR may remain in circulation at higher concentration than their high affinity counterparts, since they are not cleared from the system as efficiently as those with higher affinity for the TfR. A low or moderate affinity variant of an anti-TfR carrier antibody for instance has a binding affinity for the TfR in the range of 1-10 μM.

In one embodiment, said target binding antibody is a full-length antibody, a Fab, F(ab')$_2$ or a Fv. In one embodiment, said target binding antibody is a full length antibody.

A brain delivery protein comprising two carrier moieties as disclosed above may moreover prove advantageous from a manufacturing perspective, since the generation of an antibody based brain delivery protein comprising two identical light chains is likely to be produced in higher yields compared with the production of an antibody with two different light chains (i.e. one with and one without a linked carrier antibody).

A brain delivery protein according to the present invention may thus comprise a target binding antibody which has binding affinity for any target of interest in the mammalian, such as a human or animal, brain. The brain target may in particular be a target of interest for research purposes, therapy or diagnostics, such as a target involved in a brain disorder, in particular a neurodegenerative disorder. In one embodiment, said target in the brain is selected from amyloid β (Aβ) peptide, alpha synuclein, superoxide dismutase (SOD), huntingtin, transthyretine, β-secretase 1, epidermal growth factor, epidermal growth factor receptor 2, Tau, phosphorylated Tau, apolipoprotein E4, CD20, prion protein, leucine rich repeat kinase 2, parkin, presenilin 2, gamma secretase, death receptor 6, amyloid precursor protein, p75 neurotrophin receptor, neuregulin and caspase 6.

Alzheimer's disease (AD) is one of the most common neurodegenerative disorders. Numerous trials have been conducted with antibodies targeting the self-aggregating protein amyloid-β (Aβ). Although amyloid plaques, consisting of fibrillar deposits of Aβ, are a hallmark of AD, soluble Aβ, in particular oligomers and protofibrils, measured in post mortem AD brain tissue and CSF, have been shown to correlate better with disease progression and to be harmful to synapses and neurons. Soluble Aβ assemblies are therefore a suitable target for immunotherapy with Aβ specific antibodies. Thus, in one embodiment, said brain target is an Aβ peptide. In a particular embodiment, said Aβ peptide is soluble Aβ aggregate, preferably selected from oligomers and protofibrils. Examples of anti-Aβ antibodies that bind protofibrils, as well as methods for production thereof, are disclosed in WO 2002/03911, WO 2005/123775, WO 2007/108756, WO 2011/001366, and WO 2016/005466, the disclosures of which are hereby incorporated by reference. A well-studied mouse monoclonal antibody, referred to as mAb158, and its humanized form, referred to as BAN2401, which binds to Aβ protofibrils is disclosed e.g. in WO 2007/108756. In addition, it has no affinity for the Aβ protein precursor. Mutated variants of BAN2401 are disclosed in WO 2016/005466. RmAb158, used as a target binding antibody in the appended examples, is a recombinant version of mAb158 with identical Aβ binding properties.

There are other disorders associated with Aβ protein aggregation, such as traumatic brain injury (TBI), Lewy body dementia (LBD), Down syndrome (DS), Amyotrophic lateral sclerosis (ALS), Frontotemporal dementia, tauopathies, systemic amyloidosis, atherosclerosis and Parkinson's disease dementia (PDD). A brain delivery protein comprising a target binding antibody having affinity for an Aβ peptide may prove useful in e.g. therapy or diagnosis of such disorders.

In one embodiment, said brain delivery protein comprises an Aβ binding antibody, and two carrier moieties. The Aβ binding antibody may be an antibody having binding specificity for Aβ protofibrils, such as mAb158/BAN2401 or a mutant or variant thereof as disclosed in any one of the prior art publications specifically mentioned above. In particular embodiments, such a brain delivery protein comprises two carrier antibodies, each being linked to a C-terminal end of a (separate) light chain of the Aβ binding antibody by a linker. Each of the carrier moieties may for example be an anti-TfR antibody or a fragment thereof as defined herein, such as a scFv8D3, optionally linked by a linker as set out in SEQ ID NO:1 to the target binding moiety.

In one embodiment, said Aβ binding antibody is mAb158/BAN2401 or a mutant or variant thereof and each of said carrier moieties is a scFv8D3, wherein each of said scFv8D3 is linked to a C-terminal end of a light chain of said mAb158/BAN2401 or mutant or variant thereof, said protein optionally further comprising two linkers, each linker having an amino acid sequence as set out in SEQ ID NO:1, for linking said scFv8D3 to said said mAb158/BAN2401 or mutant or variant thereof.

In one embodiment, said brain target is alpha synuclein. Parkinson's disease (PD) and Lewy body dementia (LBD) are the two most prevalent examples of neurodegenerative disorders with alpha synuclein brain pathology. Other examples include the Lewy body variant of Alzheimer's disease, multiple system atrophy, psychosis, schizophrenia, and Creutzfeldt-Jakob disease. In one embodiment, said alpha synuclein is soluble alpha synuclein, preferably selected from oligomers and protofibrils. A target binding antibody which binds alpha synuclein may in particular have high affinity for human alpha synuclein protofibrils and low binding of alpha synuclein monomers. Specific examples of anti-alpha synuclein antibodies are disclosed in WO 2009/133521, WO 2011/104696, which are hereby incorporated by reference.

In one embodiment, said brain delivery protein comprises an alpha synuclein binding antibody, and two carrier moieties. In one embodiment, said alpha synuclein binding antibody binds human alpha synuclein protofibrils, preferably said alpha synuclein binding antibody does not bind alpha synuclein monomers. The alpha synuclein binding antibody may be an antibody or an antibody variant as disclosed in any one of the prior art references mentioned above. One example of a alpha synuclein binding antibody is mAb48, or a mutant or variant thereof. mAb48 is disclosed in WO 2011/104696 and denoted "48611/8" and described inter alia on pages 31-32 in Tables 1 and 2. In particular embodiments, such a brain delivery protein comprises two carrier antibodies, each being linked to a C-terminal end of a light chain of the alpha synuclein binding antibody by a linker. Each of the two carrier moieties may for example be an anti-TfR antibody, such as a scFv8D3, optionally linked by a linker as set out in SEQ ID NO:1 to the target binding moiety.

In one embodiment, said alpha synuclein binding antibody is mAb48 or a mutant or variant thereof and each of said carrier moieties is a scFv8D3, wherein each of said scFv8D3 is linked to a C-terminal end of a light chain of said mAb48 or mutant or variant thereof, said protein optionally further comprising two linkers, each linker having an amino acid sequence as set out in SEQ ID NO:1, for linking said scFv8D3 to said said mAb48 or mutant or variant thereof.

In one embodiment, said brain target is SOD. A brain delivery protein comprising a SOD directed antibody may be useful in e.g. treatment and diagnosis of ALS.

In one embodiment, said brain target is huntingtin. A brain delivery protein comprising an antibody directed to huntingtin may be useful in e.g. treatment and diagnosis of Huntington's disease.

In one embodiment, said brain target is transthyretin. A brain delivery protein comprising an antibody directed to transthyretin may be useful in e.g. treatment and diagnosis of familial amyloid neuropathy.

In one embodiment, said target binding antibody is a humanized antibody.

In one embodiment, said brain delivery protein is recombinant.

In one embodiment, said protein is a fusion protein. In particular, said protein may be expressed as a fusion protein.

In a related aspect there is provided an isolated nucleic acid encoding the protein according to any one of the preceding claims. An expression vector comprising such a nucleic acid may enable production of a brain delivery protein for example by expression in a host cell.

The brain delivery protein according to the invention may be useful as a therapeutic or diagnostic agent or as a research tool, e.g. as a PET or SPECT ligand. In one embodiment, said brain delivery protein is for use in prophylaxis or therapy. For example, said brain delivery protein is for use in treatment and/or prophylaxis of a brain disorder such as a neurodegenerative disorder.

In one embodiment, said brain delivery protein is for use in treatment and/or prophylaxis of a neurodegenerative disorder selected from the group consisting of Alzheimer's disease and other disorders associated with Aβ protein aggregation, such as traumatic brain injury (TBI), Lewy body dementia (LBD), Downs syndrome (DS), Amyotrophic lateral sclerosis (ALS), Frontotemporal dementia, tauopathies, systemic amyloidoses, atherosclerosis and Parkinson's disease dementia (PDD); the Lewy body variant of Alzheimer's disease; multiple system atrophy; psychosis; schizophrenia; Creutzfeldt-Jakob disease; Huntington's disease, and Familial amyloid neuropathy.

In one embodiment, said brain delivery protein is for use in treatment and/or prophylaxis of Alzheimer's disease. In particular, such a brain delivery protein comprises a target binding protein which binds to Aβ peptide, preferably a soluble form of an Aβ peptide such as oligomers and/or protofibrils.

In one embodiment, said brain delivery protein is for use in treatment and/or prophylaxis of Parkinsons's disease. In particular, such a brain delivery protein comprises a target binding protein which binds alpha synuclein, preferably a soluble form of alpha synuclein, such as oligomers and/or protofibrils.

In one embodiment, said brain delivery protein is for use in in vivo diagnostics. For example, said brain delivery protein is for use in in vivo diagnostics of a brain disorder such as a neurodegenerative disorder.

In one embodiment, said brain delivery protein is for use in in vivo diagnostics of a neurodegenerative disorder selected from the group consisting of Alzheimer's disease and other disorders associated with Aβ protein aggregation, such as traumatic brain injury (TBI), Lewy body dementia (LBD), Downs syndrome (DS), Amyotrophic lateral sclerosis (ALS), Frontotemporal dementia, tauopathies, systemic amyloidoses, atherosclerosis and Parkinson's disease dementia (PDD); the Lewy body variant of Alzheimer's disease; multiple system atrophy; psychosis; schizophrenia; Creutzfeldt-Jakob disease; Huntington's disease, and familial amyloid neuropathy.

In one embodiment, said brain delivery protein is for use in in vivo diagnostics of Alzheimer's disease. In particular, such a brain delivery protein comprises a target binding protein which binds to Aβ peptide, preferably a soluble form of an Aβ peptide such as oligomers and/or protofibrils.

In one embodiment, said brain delivery protein is for use in treatment of Parkinsons's disease. In particular, such a brain delivery protein comprises a target binding protein which binds alpha synuclein, preferably a soluble form of alpha synuclein, such as oligomers and/or protofibrils.

In one embodiment, said brain delivery protein is for use in in vivo diagnostics using PET.

In one embodiment, said brain delivery protein further comprises a label enabling detection of said protein in the brain. In this context a label should be understood as a marker which is coupled to the brain delivery protein and which is intended for use in detection and/or imaging for inter alia medical, diagnostic or research purposes. The label may be coupled either to the target binding antibody or to one of the carrier moieties. Non-limiting examples of such labels include radiolabel, a fluorophore, a chromophore, or an affinity tag. In one embodiment, the label is a radiolabel used for medical or diagnostic imaging, for example $Zr^{89}$, $I^{124}$, $I^{125}$, $I^{131}$, $C^{11}$, $C^{14}$, $H^3$, $F^{18}$, or $Gallium^{68}$, suitable for use in SPECT (Single-photon emission computed tomography) or PET (Positron Emission Tomography) imaging.

The brain delivery protein as disclosed herein is suitably directed to a target in the mammalian brain. Thus, the brain delivery protein of the present invention is suitable for therapeutic or diagnostic use in a mammal. A mammal as used herein includes, but is not limited to, domesticated animals (e.g. cows, sheep, cats, dogs, and horses), primates (e.g. humans and non-human primates such as monkeys), rabbits, and rodents (e.g. mice and rats). In certain embodiments, the mammal is a human.

In a related aspect, there is provided a pharmaceutical composition comprising a brain delivery protein according to the present invention and a pharmaceutically acceptable carrier. In a specific embodiment for therapeutic use, the compositions are physiologically acceptable formulations comprising a therapeutically active amount of a brain delivery protein according to the invention in a physiological buffer suitable for administration to humans and/or animals. The brain delivery protein can be freeze dried for better stability. The freeze dried formulation may contain any suitable conventional excipients, including stabilizers, lyoprotectants, buffers, and the like, such as, but not limited to, mannitol, for protecting and/or stabilizing the product during and/or after freeze drying and/or subsequent storage.

In a related aspect, there is provided a method for treatment and/or prophylaxis of a brain disorder in a mammal having, or being at risk of developing said disorder, comprising administering to said mammal a therapeutically effective amount of the brain delivery protein according to the invention. In particular, said disorder is a neurodegenerative disorder selected from the group consisting of Alzheimer's disease and other disorders associated with Aβ protein aggregation, such as traumatic brain injury (TBI), Lewy body dementia (LBD), Downs syndrome (DS), Amyotrophic lateral sclerosis (ALS), Frontotemporal dementia, tauopathies, systemic amyloidoses, atherosclerosis and Parkinson's disease dementia (PDD); the Lewy body variant of Alzheimer's disease; multiple system atrophy; psychosis; schizophrenia; Creutzfeldt-Jakob disease; Huntington's disease, and familial amyloid neuropathy. As disclosed above, particular target binding antibodies may be useful in treatment of certain neurodegenerative disorders due to their binding affinity for certain brain targets. The embodiments as disclosed for related aspects of the present invention are thus equally relevant also for the method of treatment aspect of the invention.

In a related aspect, there is provided a method for diagnosing and/or detecting a brain disorder in a mammal suspected of having, or being at risk of developing said disorder, comprising administering to said mammal the brain delivery protein according to the invention in an amount sufficient to enable diagnosis and/or detection. In a particular embodiment, said disorder is a neurodegenerative disorder such as a neurodegenerative disorder selected from the group consisting of Alzheimer's disease and other disorders associated with Aβ protein aggregation, such as traumatic brain injury (TBI), Lewy body dementia (LBD), Downs syndrome (DS), Amyotrophic lateral sclerosis (ALS), Frontotemporal dementia, tauopathies, systemic amyloidoses, atherosclerosis and Parkinson's disease dementia (PDD); the Lewy body variant of Alzheimer's disease; multiple system atrophy; psychosis; schizophrenia; Creutzfeldt-Jakob disease; Huntington's disease, and familial amyloid neuropathy. As disclosed above, particular target binding antibodies may be useful in diagnosis or detection of certain disorders due to their binding affinity for certain brain targets. It should be understood that specific embodiments of the method for diagnosing and/or detecting may be in vivo or in vitro methods, such as in vivo diagnostics in the brain of a mammal or such as in vitro diagnostics of a cell sample. The embodiments as disclosed for related aspects of the present invention are thus equally relevant also for the aspect of diagnosing/detecting as disclosed above.

The invention will be further illustrated by the following non-limiting examples.

BRIEF DESCRIPTION OF THE DRAWINGS

FIG. 1A shows a brain delivery protein comprising two carrier moieties, represented by scFvs, attached by linkers to the C-terminal of the two light chains of target binding antibody, represented by an antibody. FIG. 1B depicts the presumed monovalent binding of the brain delivery protein to a receptor expressed on a BBB endothelial cell.

FIG. 4A shows the ex vivo quantified brain concentration of a specific example of a brain delivery protein as disclosed herein, [$^{124}$I]RmAb158-scFv8D3, in old (18-24 months) and young (8-9 months) wt and tg-ArcSwe mice 3 days post injection. FIG. 4B shows a comparison of ex vivo brain concentration of a chemically fused 8D3-F(ab')$_2$-mAb158 and RmAb158-scFv8D3 in 18 months old tg-ArcSwe mice 3 days post injection. FIG. 4C shows ex vivo quantified brain concentration of [$^{124}$I]RmAb158-scFv8D3 in old (18-24 months) tg-ArcSwe mice at 3, 6 and 10 days post administration in comparison with blood concentration over the same time period. Elimination from brain was much slower than elimination from blood.

EXAMPLES

Figure 1:
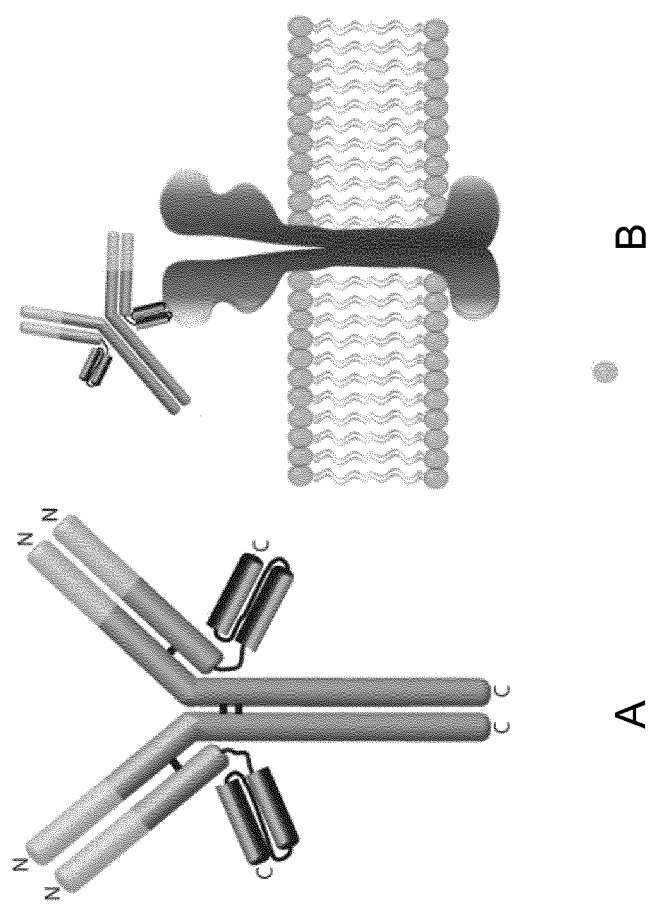
FIG. 1 is a schematic representation of an embodiment of a brain delivery protein according to the present invention.

Example 1: Generation and Characterization of a Recombinant Bispecific Aβ-TfR Antibody Cloning of RmAb158-scFv8D3

Both the heavy and light chains of the expressed antibody were cloned into the vector pcDNA3.4 (ThermoFischer)

with signal peptides on the N-terminal. The 8D3 sequence (Boado et al, supra) was made into a scFv with the heavy chain variable fragment as the N-terminal part and the light chain variable fragment on the C-terminal. The heavy and light chains were separated by an 18 aa long GlySer-rich amino acid linker (GSTSGGGSGGGSGGGGSS, SEQ ID NO:2), previously disclosed in Wu A M. et al, Protein Eng. 14: 1025-1033 (2001). The scFv 8D3 was then connected to the C-terminal of light chain of RmAb158 (e.g. disclosed in EP 2004688) with an in house designed peptide linker having the amino acid sequence APGSYTGSAPG (SEQ ID NO:1). Prolines were added at the beginning and at the end of the linker to ensure that alpha helixes were not extended, since they cannot donate the amide hydrogen bond needed in alpha helixes. Polar amino acids like serine and threonine were added to ensure that the linker was hydrophilic, and the smaller amino acid glycine was added to ensure flexibility.

Expression and Purification of RmAb158-scFv8D3

The recombinant fusion protein was expressed using the protocol described in "Protein Expression in Mammalian Cells: Methods and Protocols" (Baldi L. et al, Methods in Molecular Biology, 81:13-26 (2012)) except that the cells, the medium for cell culture and the vector were replaced with the ones mentioned in the following: Expi293 cells (ThermoFisher) were grown in Expi293 medium (ThermoFisher) and transiently transfected with the heavy chain and the light chain pcDNA3.4 vectors with the use of polyethyleneimine (PEI) as transfection reagent and valproic acid (VPA) as a cell cycle inhibitor. RmAb158-scFv8D3 was purified on a HiTrap protein G column (GE Healthcare), and eluted with a gradient to 0.7% HAc.

In Vitro Analysis of RmAb158-scFv8D3

To confirm the size and integrity of RmAb158-scFv8D3, the fusion protein was analyzed with SDS-PAGE. RmAb158 and RmAb158-scFv8D3 were mixed with Bolt® LDS sample buffer, without reducing agent, and directly loaded onto a 10% Bolt Bis-Tris Plus gel (Thermo Fisher) and run for 22 min at 200 V, washed in dH$_2$O and stained with Page blue (Fermentas). A Chameleon pre-stained protein marker (Li-Cor) was used as a molecular weight standard.

To assess specific binding to Aβ monomers and protofibrils in solution, RmAb158-scFv8D3 was analyzed with an inhibition ELISA in comparison with the Aβ antibody 6E10 (Covance), as previously described (Englund H. et al, J. Neurochem. 103: 334-345 (2007)). 96-well plates were coated for 2 h at +4° C. with 45 ng/well of Aβ protofibrils, followed by 1 h blocking with BSA. Serially diluted Aβ monomers or protofibrils were pre-incubated 1 h with a fixed concentration of antibody (RmAb158-scFv8D3-50 ng/ml; 6E10-400 ng/ml) in a non-binding 96-well plate. The Aβ-antibody solution was then transferred to the Aβ coated plates and incubated for 15 min, followed by detection with horseradish peroxidase (HRP) conjugated anti-mouse-IgG-F(ab')$_2$ (Jackson ImmunoResearch Laboratories, West Grove, Pa., USA) and K blue aqueous TMB substrate (Neogen Corp., Lexington, Ky., USA) and read with a spectrophotometer at 450 nm. All Aβ and antibody dilutions were made in ELISA incubation buffer (PBS with 0.1% BSA, 0.05% Tween, and 0.15% Kathon). Aβ monomer and protofibril preparations were made as previously described (Magnusson K. et al, J. Alzheimers Dis. 37: 29-40 (2013)).

A competition ELISA was used to assess the ability of RmAb158-scFv8D3 to bind to TfR in comparison with a previously generated chemically fused 8D3-F(ab')2-h158 (Sehlin D. et al, supra (2016)), 8D3 and a scFv fragment of 8D3. 96-well plates were coated over night at +4° C. with 50 ng/well of recombinant transferrin receptor protein (Sinobiological, Beijing, China) and blocked with BSA. Serially diluted antibody was incubated on the plates for 2 h on a shaker in competition with 2.5 nM of biotinylated scFv8D3, then detected with horseradish peroxidase (HRP) conjugated streptavidin (Mabtech AB, Nacka Strand, Sweden) and K blue aqueous TMB substrate (Neogen Corp., Lexington, Ky., USA) and read with a spectrophotometer at 450 nm. All antibody dilutions were made in ELISA incubation buffer (PBS with 0.1% BSA, 0.05% Tween, and 0.15% Kathon). All Aβ and antibody dilutions were made in ELISA incubation buffer. IC50 and Kd values were estimated with non-linear regression analyses using GraphPad Prism 5.0 (GraphPad Software, Inc, La Jolla, Calif., USA).

Results

A single chain variable fragment (scFv), comprising the heavy and light chain variable regions of 8D3 connected to each other by a linker, was attached to the C-terminus of each of the RmAb158 light chains via a short peptide linker (FIG. 1A). This linker was designed to avoid formation of alpha helices, and the number of hydrophilic amino acids was selected to avoid formation of a hydrophobic core. Amino acids with small side chains were incorporated in the linker to ensure flexibility. The purpose of the short length of the linker was to tie the scFv closely to RmAb158, so that a bivalent binding to TfR would be sterically difficult (FIG. 1B).

Protein expression in Expi293 cells resulted in yields around 15-30 mg antibody per liter of transfected cell culture. The purified protein was analyzed with SDS-PAGE on which a single band was observed (results not shown), i.e. RmAb158-scFv8D3 was pure and the same batch was used in all in vitro and in vivo studies described below.

Figure 2:
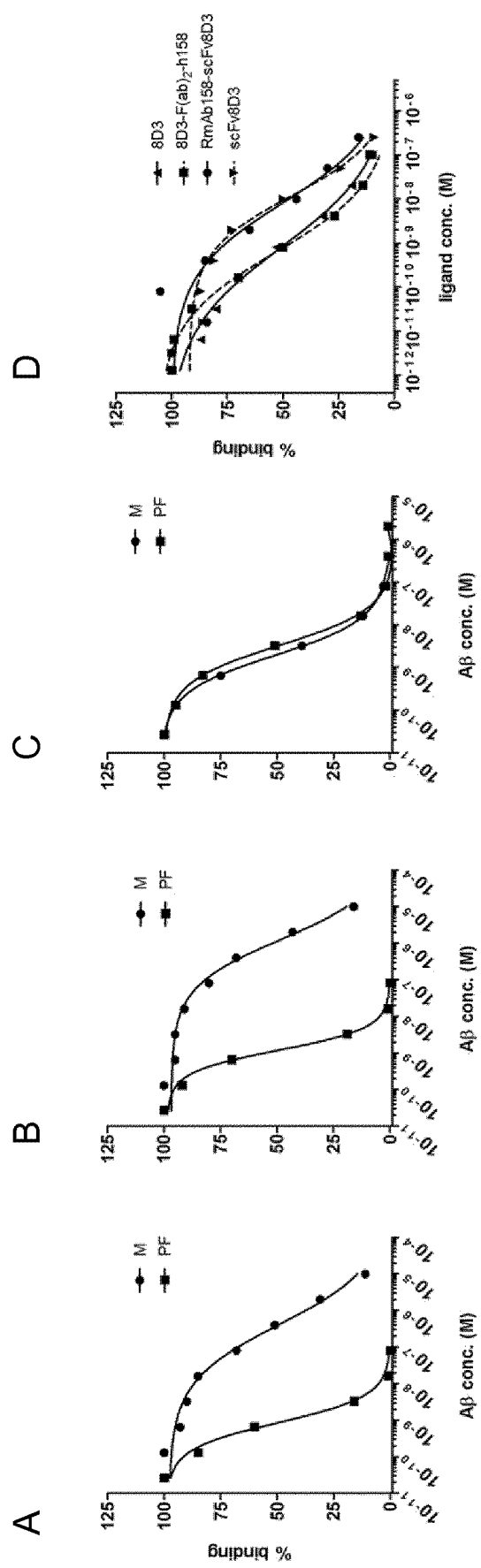
FIG. 2A-C show results from inhibition ELISA, displaying that RmAb158-scFv8D3, an example of a brain delivery protein according to the present invention, retains a high selective binding to Aβ protofibrils (PF) over monomers (M) (2A) comparable to RmAb158 (2B), whereas the control antibody 6E10 binds equally well to both Aβ species (2C).
FIG. 2D shows results from a TfR competition ELISA, demonstrating that the anti-TfR antibody 8D3, as well as a chemically conjugated fusion protein 8D3-F(ab')$_2$-h158 (Sehlin et al, 2016, supra), which can both bind bivalently to TfR, display almost 10-fold stronger binding to TfR compared with RmAb158-scFv8D3, which is a specific example of a brain delivery protein according to the present invention. A scFv fragment of 8D3 has an even weaker TfR binding, since it has only one binding site.

To assess the functionality of the generated fusion protein, in vitro binding analyses were performed. The fusion protein's selectivity to different Aβ species was studied with an inhibition ELISA, where the ability of Aβ monomers and protofibrils to inhibit the signal in an indirect Aβ ELISA approximates the affinity to the tested antigen. RmAb158-scFv8D3 showed a near 500-fold stronger binding to protofibrils than to monomers, with median inhibitory concentrations (1050) of 0.85 and 400 nM, respectively (FIG. 2A), similar to RmAb158, with 1050 of 1.2 nM for monomers and 1.2 µM for protofibrils (FIG. 2B). The widely used Aβ antibody 6E10 served as control, displaying no difference in binding to the different Aβ preparations (FIG. 2C).

TfR binding was assessed with a competition TfR ELISA (FIG. 2D), where plates were coated with a high concentration of recombinant TfR protein to mimic the possibility to achieve a bivalent binding, with higher avidity as a read-out for that. A biotinylated scFv of 8D3 was subjected to competition by serially diluted scFv8D3, RmAb158-scFv8D3, 8D3 and chemically fused 8D3-F(ab')$_2$-h158. As predicted, RmAb158-scFv8D3 displayed a 10-fold lower avidity compared with the entire 8D3 antibody and 8D3-F(ab')2-h158, with estimated Kd values of 8.0, 0.80 and 0.69 nM respectively. ScFv8D3, which is monovalent by definition, displayed a Kd value of 15 nM, i.e. approximately 2-fold higher than RmAb158-scFv8D3. Since the recombinant fusion protein has two possible binding sites per molecule, there is no actual difference in binding between scFv8D3 and RmAb158-scFv8D3, strongly suggesting a monovalent interaction with TfR.

Example 2: In Vivo Studies of Brain Distribution and Peripheral Biodistribution with Radiolabeled RmAb158-scFv8D3

Animals

Tg-ArcSwe model, harbouring the Arctic (AβPP E693G) and Swedish (AβPP KM670/671NL) mutations and maintained on a C57BL/6 background (Lord, A. et al, Neurobiol Aging 27, 67-77 (2006); Philipson, O. et al, Neurobiol Aging 30, 1393-1405 (2009)), show elevated levels of soluble Aβ protofibrils already at a very young age and abundant and rapidly developing plaque pathology starting at around 6 months of age. Both males and females were used and littermates were used as control animals (wt). The animals were housed with free access to food and water in rooms with controlled temperature and humidity in an animal facility at Uppsala University. All procedures described herein were approved by the Uppsala County Animal Ethics board (#C17114), following the rules and regulations of the Swedish Animal Welfare Agency and were in compliance with the European Communities Council Directive of 22 September 2010 (2010/63/EU).

Radiochemistry

The bispecific RmAb158-scFv8D3 was labelled with iodine-125 ($^{125}$I) for ex vivo experiments and iodine-124 ($^{124}$I) for PET experiments using direct radioiodination (Greenwood, F. C. et al, Biochem. J. 89,114-123 (1963)). The method is based on electrophilic attack of the phenolic ring of tyrosine residues by in situ oxidized iodine. Briefly, for $^{125}$I-labelling, 120 pmoles of antibody or fusion protein (assumed Mw 210 kDa), $^{125}$I stock solution (Perkin-Elmer Inc., Waltham, Mass., USA) and 5 μg Chloramine-T (Sigma Aldrich, Stockholm, Sweden) were mixed in PBS to a final volume of 110 μl. The reaction was allowed to proceed for 90 s and subsequently quenched by addition of double molar excess of sodium metabisulfite (Sigma Aldrich) and dilution to 500 μl in PBS. For $^{124}$I-labelling, 60 μl $^{124}$I stock solution (Perkin-Elmer Inc.) was pre-incubated 15 min with 12 μl 50 μM NaI before addition of 240 μmoles of fusion proteins and 40 μg Chloramine-T, mixed in PBS to a final volume of 420 μl. The reaction was allowed to proceed for 120 s and subsequently quenched by addition of 80 μg of sodium metabisulfite in PBS. The radiolabeled proteins were purified from free iodine and low-molecular weight components with a disposable NAP-5 size exclusion column, Mw cut-off 5 kDa (GE Healthcare AB, Uppsala, Sweden), according to the manufacturer's instructions and eluted in 1 ml of PBS. The yield was calculated based on the added radioactivity and the radioactivity in the purified radioligand solution. Labelling was performed less than 2 h prior to each study.

Ex Vivo Studies

Mice were intravenously (i.v.) injected with 0.44±0.03 MBq [$^{125}$I]RmAb158 (n=3) or 0.89±0.26 MBq [$^{125}$I]RmAb158-scFv8D3 (n=10), which equals a dose of 0.05 mg/kg. Blood samples (8 μl) were obtained from the tail vein at 0.5, 1, 2, 3, 4, 6, 8, 24 and 48 h after injection. A subset of animals (n=3 for each ligand) were euthanized 2 h after injection while the rest were euthanized at 3 days post injection. A separate group of wt mice were injected with 10 mg/kg RmAb158 (n=5) and 13.3 mg/kg RmAb158-scFv8D3 (n=5), containing 1.5% radiolabeled protein for detection, and euthanized 2 h after injection. After perfusion, the brain was isolated and the cerebellum was separated from the rest of the brain before the brain tissue samples were frozen on dry ice. Liver, lung, heart, spleen, kidney, pancreas, muscle and femur was also isolated. Radioactivity in blood, brain, cerebellum and isolated organs was measured with a γ-counter (1480 Wizard™, Wallac Oy, Turku, Finland). The brain, cerebellum and blood concentrations, quantified as % of injected dose per gram tissue (% ID/g), were calculated as following:

% ID/g=Measured radioactivity per gram tissue (or blood)/Injected radioactivity

In addition, the tissue-to-blood ($K_p$) concentration ratio was calculated as following:

$K_p$=Measured radioactivity per gram tissue/Measured radioactivity per gram blood PET Studies The day before injection of [$^{124}$I]RmAb158-scFv8D3 animals were given water supplemented with 0.2% NaI to reduce thyroidal uptake of $^{124}$I. Mice (n=12) were intravenously (i.v.) injected with 7.2±3.4 MBq [$^{124}$I]RmAb158-scFv8D3, corresponding to a dose of 0.5 mg/kg. Blood samples (8 μl) were obtained from the tail vein at 1, 3, 6, 24 and 48 h after injection. At 3 days post injection the animal was placed in the gantry of the animal PET/CT scanner (Triumph Trimodality System, TriFoil Imaging, Inc., Northridge, Calif., USA) and scanned in list mode during 60 min followed by a CT examination for 3 min (Field of View (FOV)=8.0 cm). Animals were euthanized after the PET scans according to the same procedure as described above for the ex vivo studies including a terminal blood sample from the heart. Radioactivity in blood, brain, cerebellum and isolated organs was measured with a well counter (GE Healthcare, Uppsala, Sweden). Two animals were scanned at 6 days post injection and one animal was scanned at 10 days post injection.

The PET data were reconstructed using the ordered subsets expectation-maximization (OSEM) 3D algorithm (20 iterations). The CT raw files were reconstructed using Filter Back Projection (FBP). All subsequent processing of the PET and CT images were performed in imaging software Amide 1.0.4 (Loening A M. et al, Mol. Imaging 2: 131-137 (2003)). The CT scan was manually aligned with a T2 weighted, MRI based mouse brain atlas (Ma Y, et al, Neuroscience 135: 1203-1215 (2005)) containing outlined regions of interests for hippocampus, striatum, thalamus, cortex and cerebellum. The PET image was then aligned with the CT, and thus, the MRI-atlas was also aligned with the PET data.

Results

RmAb158-scFv8D3 was radiolabeled with $^{125}$I and $^{124}$I in yields around 70% for in vivo studies in mice. The specific activity was 0.4±0.1 MBq/μg (79±19 MBq/nmol) for [$^{125}$I]

RmAb158-scFv8D3 and 1.2±0.7 MBq/μg (261±145 MBq/nmol) for [$^{124}$I]RmAb158-scFv8D3.

To test the ability of the scFv8D3 moiety to enable TfR mediated transcytosis in vivo, wt mice were administered with [$^{125}$I]RmAb158 or [$^{125}$I]RmAb158-scFv8D3 and the brains were isolated 2 h after injections. The brain concentrations, expressed as percent of injected dose per gram brain tissue (% ID/g, Equation 1) was 0.03±0.01 and 2.20±0.92 for [$^{125}$I]RmAb158 and [$^{125}$I]RmAb158-scFv8D3, respectively (FIG. 3A). Thus, the scFv8D3 modification lead to an 80-fold increase in brain concentrations at this time point. The brain-to-blood concentration ratio (Kp, see equation above) was 0.0010±0.00013 and 0.15±0.10 for the two ligands, respectively (FIG. 3B). Hence the Kp, which takes into account available ligand in blood, was increased 140-fold by the scFv8D3 modification of RmAb158.

To further investigate the pharmacokinetics and brain distribution, radiolabeled RmAb158-scFv8D3 was administered to young (8-9 months) and old (18-24 months) wt and tg-ArcSwe mice. The majority (n=14) of the mice were euthanized at 3 days post injection, while two old tg-ArcSwe mice were kept under investigation until 10 days after injection and one old tg-ArcSwe was euthanized at day 14 after injection.

Figure 4:
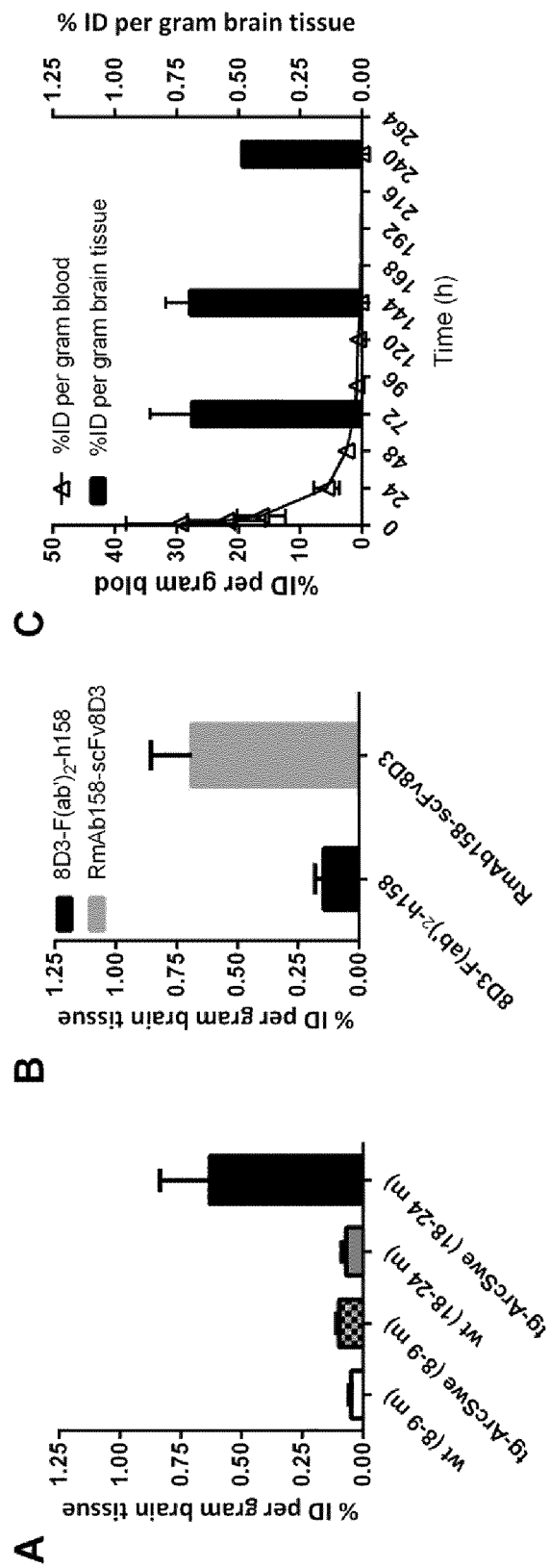
FIG. 4A-C are diagrams displaying the results from ex vivo experiments.

Three days after administration of RmAb158-scFv8D3, a 9-fold higher brain concentration of fusion protein was found in old tg-ArcSwe mice (% ID/g=0.69±0.17) compared with old wt mice (% ID/g=0.08±0.01) (FIG. 4A). This equals a 5-fold difference in comparison with the chemically generated fusion protein 8D3-F(ab')$_2$-h158 (FIG. 4B). The brain concentrations of RmAb158-scFv8D3 decreased only slightly during the next 7 days after administration (FIG. 4C). The half-life in blood based on samples obtained between 3 h and 3 days was 18.6±1.5 h. From 1 day to 3 days, i.e. during the elimination phase, the half-life was 24.4±3.3 h (FIG. 4C). There was no difference in blood concentrations or half-life between transgenic and wt mice.

Figure 5:
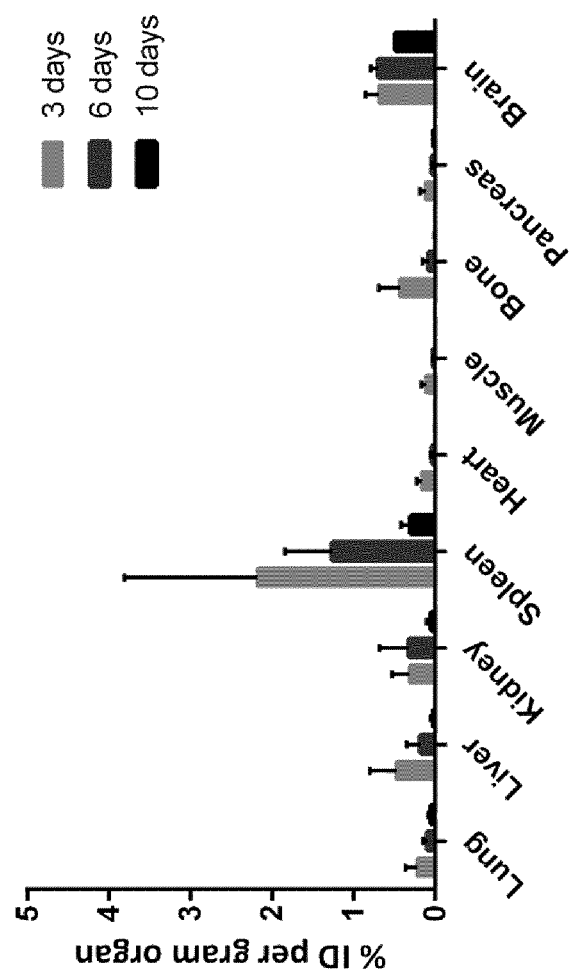
FIG. 5 is a diagram showing the biodistribution of a specific example of a brain delivery protein as disclosed herein, [$^{124/125}$I]RmAb158-scFv8D3, quantified as percent of injected dose per organ weight in different peripheral organs at 3, 6 and 10 days after administration. Brain concentrations from FIG. 4C are included for comparison.

The distribution of [$^{125/124}$I]RmAb158-scFv8D3 in peripheral organs is shown in FIG. 5. The tissue concentrations in most organs decreased somewhat faster than the concentrations in blood. Spleen displayed the highest uptake and although the concentrations in the spleen decreased, the decrease was slower than the elimination of [$^{125/124}$I]RmAb158-scFv8D3 from the other organs (but still faster than elimination from blood).

Figure 6:
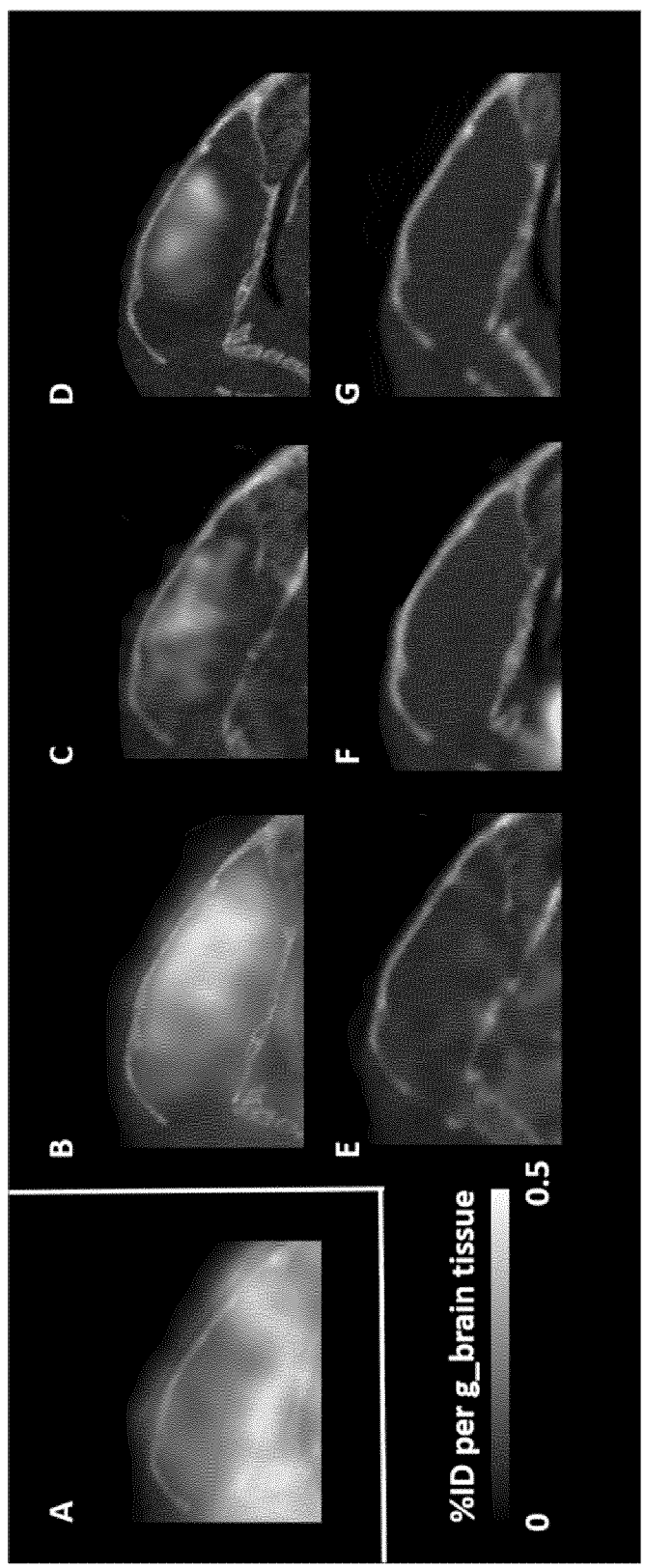
FIG. 6 shows PET images obtained during 60 min of PET scanning of a transgene-ArcSwe mouse (A-D) and of a wild type mouse (E-G). All images except (A) are displayed using the same color scale. 6A displays a PET image in an old tg-ArcSwe mouse obtained at 0-60 min post administration of [$^{124}$I]RmAb158-scFv8D3. Radioactivity concentration is similar in all brain regions. The same scale as in the other figures could not be used as the radioactivity was much higher during this early time point. PET images obtained in an old tg-ArcSwe mouse 3 days (6B), 6 days (6C) and 10 days (6D) post injection of [$^{124}$I]RmAb158-scFv8D3. PET images obtained in an old wild-type mouse 3 days (6E), 6 days (6F) and 10 days (6G) post injection of [$^{124}$I]RmAb158-scFv8D3. (% ID per g_brain tissue=percent of injected dose measured in one gram of brain tissue, i.e. a measure of brain concentrations of [$^{124}$I]RmAb158-scFv8D3).

A subset of the studied animals was PET-scanned at the time of injection, at 3, 6 or 10 days post injection. PET images from these scans are displayed in FIG. 6, demonstrating that [$^{124}$I]RmAb158-scFv8D3 is retained in tg-ArcSwe mouse brain while it is washed out from the brain of wild-type mice. PET data acquired during the first 0-60 min after injection were quantified in relation to a blood sample obtained directly after the scan, under the assumption that 3% of the brain volume is blood. This experiment showed that 72% of the PET signal at this time point was derived from [$^{124}$I]RmAb158-scFv8D3 associated with the brain tissue, suggesting a high concentration in brain was obtained almost immediately following injection (FIG. 6A). This is indicative of active transport into the brain, unlike unmodified mAb158 which has a peak in brain concentration 3 days' post injection (Magnusson K. et al, supra). Three days after injection, the recombinant fusion protein concentration had decreased to about 25% and to 10% of what had been observed in the scan at injection time in the brains of tg-ArcSwe and wt mice, respectively (FIGS. 6B and E). At later time points the brain concentrations the brain concentrations measured by PET was only somewhat decreased in old tg-ArcSwe animals (FIG. 6C-D) while there was almost no [$^{124}$I]RmAb158-scFv8D3 left in the brain of wt mice (FIG. 6F-G). Because of the brain's relatively high content of blood, the PET signal in the brain is influenced by the blood concentration of recombinant fusion protein, which decreases significantly during the first three days after injection, thus explaining the large drop in PET signal between the first and second scans. This suggests that [124I] RmAb158-scFv8D3 that is not bound to Aβ in the brain is in equilibrium with blood and is actively transported out of the brain.

Figure 7:
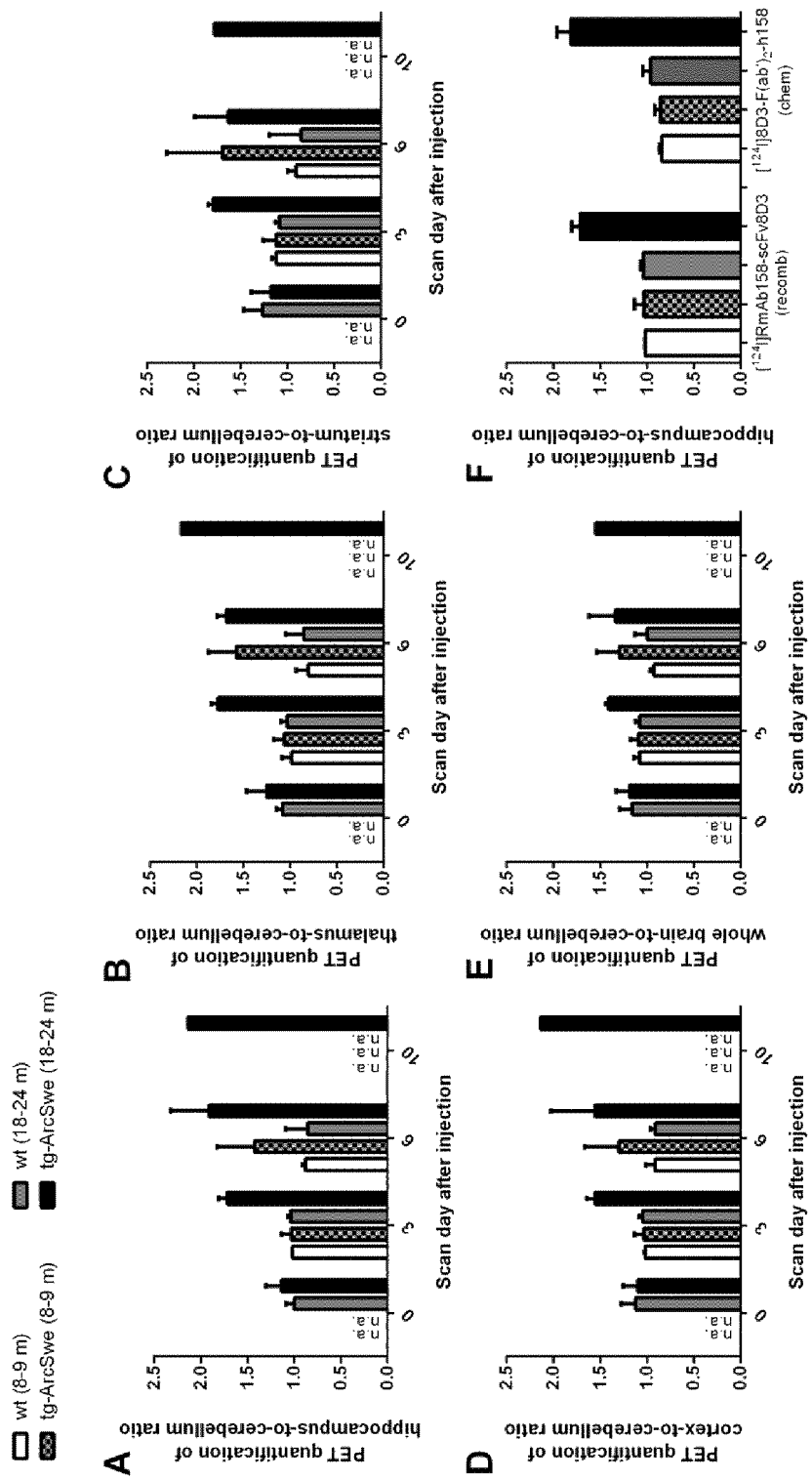
FIG. 7A-F are diagrams showing PET based brain region-to-cerebellum concentration ratios in hippocampus (A), thalamus (B), striatum (C), cortex (D) and whole brain (E). A comparison to chemically conjugated fusion protein is shown in (F). Some animal types, marked n.a. in the figure, have not been investigated at all time points.

PET data of Aβ levels in the brain, assessed with e.g. [$^{11}$C]PIB, is often quantified as the brain-to-cerebellum concentration ratio, as the cerebellum is largely spared from Aβ pathology and can act as a reference region. The concentration ratios, using cerebellum as the reference, of whole brain, thalamus, striatum, hippocampus and cortex, quantified by PET, are shown in FIG. 7. There was a clear distinction already at three days post injection with no overlap in ratios between old tg-ArcSwe and the other groups. At six days post injection, both young and old tg-ArcSwe mice could be distinguished from wt mice without protofibril accumulation in the brain. This suggests that the [$^{124}$I] RmAb158-scFv8D3 binding in the brain is indeed specific to the Aβ pathology, as previously proven for the chemical fusion protein (Sehlin D. et al, supra (2016)).

Figure 3:
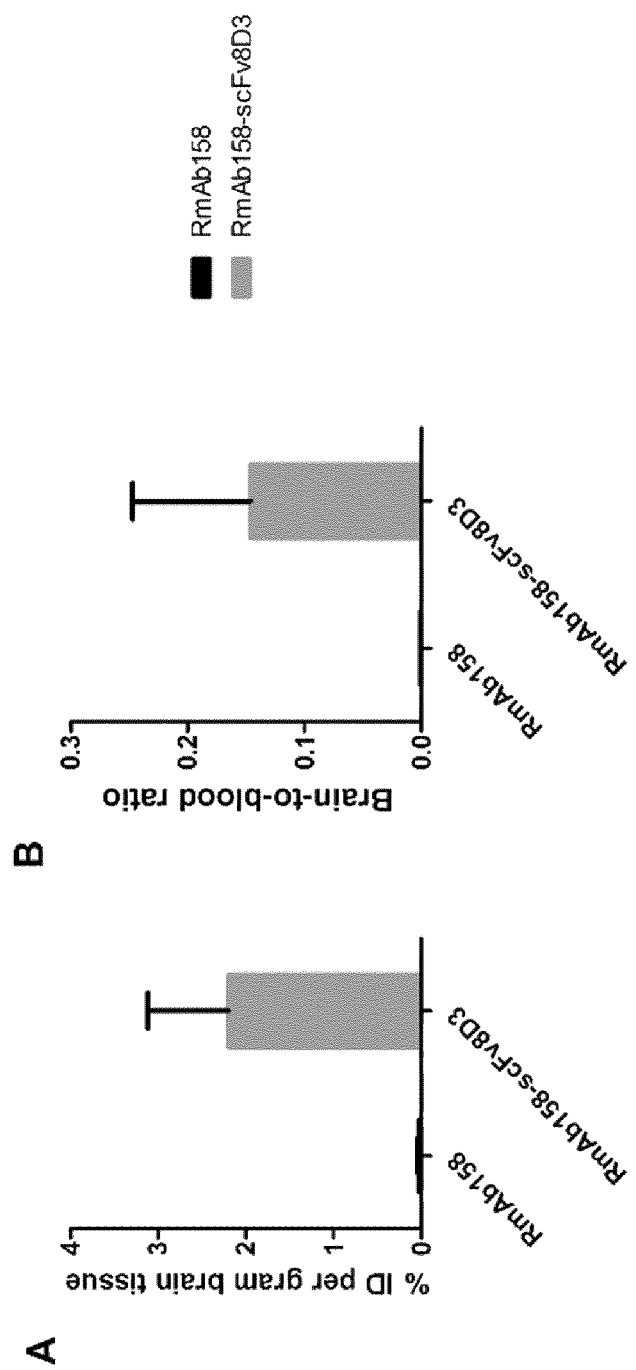
FIG. 3A-B are diagrams displaying the results from ex vivo experiments. The diagram of FIG. 3A displays that the brain concentration of [$^{125}$I]RmAb158-scFv8D3 is 80-fold higher than the brain concentration of [$^{125}$I]RmAb158 in wt mice 2 h post injection of a trace dose. [$^{125}$I]RmAb158-scFv8D3 is a labelled variant of a brain delivery protein according to the present invention, which in this experiment was administered at a trace dose. The diagram of FIG. 3B shows the brain-to-blood concentration ratio of the same proteins in the same experiment.
Figure 8:
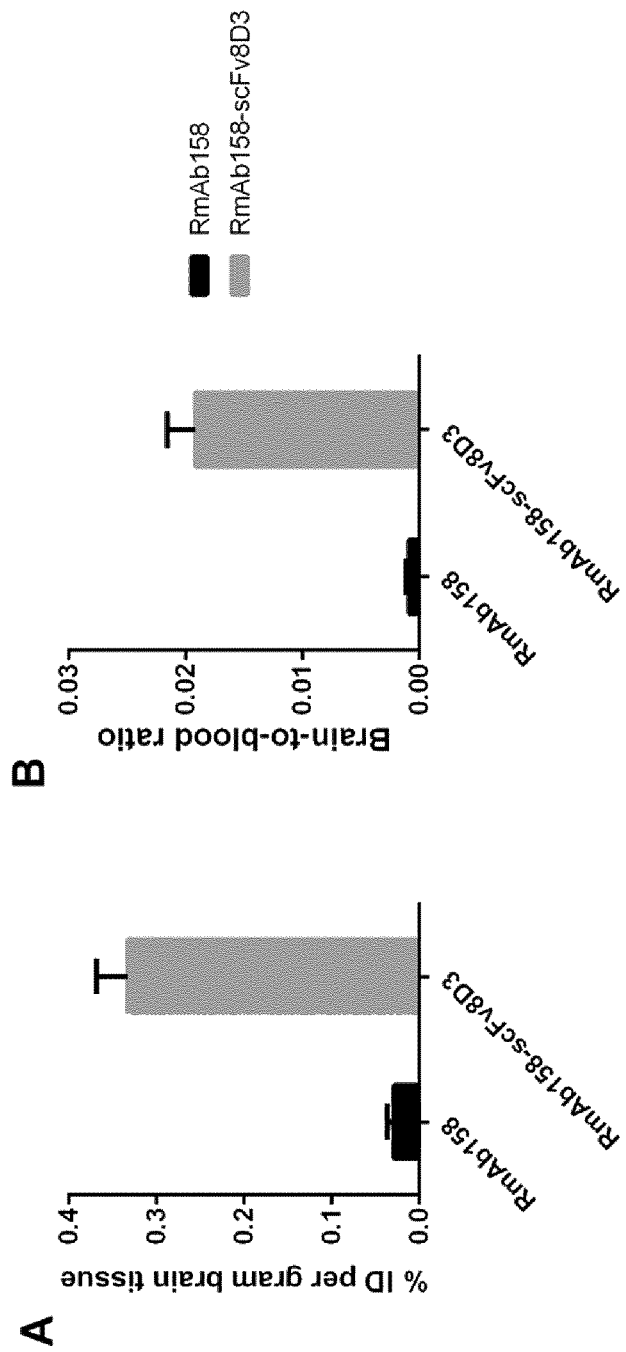
FIG. 8A-B are diagrams displaying the results from ex vivo experiments. The diagram of FIG. 8A displays that the brain concentration of [$^{125}$I]RmAb158-scFv8D3 in wt mice 2 h post injection. [$^{125}$I]RmAb158-scFv8D3 is a labelled variant of a brain delivery protein according to the present invention, which in this experiment was administered at a therapeutic dose. The diagram of FIG. 3B shows the brain-to-blood concentration ratio of the same protein administered at a trace dose.

All the 2 h brain uptake experiments described above were carried out using tracer doses of RmAb158 or RmAb158-scFv8D3, i.e. around 0.05 mg/kg. A second set of experiments was carried out using the same amount of radioactivity as in the earlier experiments but with the addition of unlabeled RmAb158 or RmAb158-scFv8D3 at doses of 10 mg/kg. The brain concentrations of RmAb158 after therapeutic dosing, expressed as % ID/g brain and brain-to-blood concentration ratio (FIG. 8), was the same as those obtained after tracer dosing (FIG. 3). Hence, the transport across the BBB was linear with dose. However, for RmAb158-scFv8D3 the TfR mediated BBB seemed to be saturated yielding lower brain concentrations in relation to dose and systemic concentrations.

Example 3: Treatment of AβPP-Transgenic Mice with RmAb158-scFv8D3

Animals

Also in this study, the AβPP transgenic mouse model tg-ArcSwe, harbouring the Arctic (AβPP E693G) and Swedish (AβPP KM670/671NL) mutations, maintained on a C57BL/6 background were used. Both males and females were used and littermates were used as control animals (wt). The animals were housed with free access to food and water in rooms with controlled temperature and humidity in an animal facility at Uppsala University. All procedures described in this paper were approved by the Uppsala County Animal Ethics Board (#C17114), following the rules and regulations of the Swedish Animal Welfare Agency, and were in compliance with the European Communities Council Directive of 22 Sep. 2010 (2010/63/EU). All efforts were made to minimize animal suffering and to reduce the number of animals used.

Antibodies and Radiolabeling

In this study, RmAb158-scFv8D3, produced as described above, and RmAb158 (BioArctic AB, Stockholm, Sweden) were used either unmodified or radiolabeled with iodine-125 ($^{125}$I).

Antibodies were labeled with $^{125}$I using direct radioiodination essentially as described in Example 2.

Ex Vivo Autoradiography

To visualize antibody distribution in the brain with ex vivo autoradiography, 18 months old tg-ArcSwe and wt mice were injected with 3.5 MBq [$^{125}$I]RmAb158-scFv8D3 or 2.9 MBq [$^{125}$I]RmAb158, equivalent to a dose of 0.20 mg IgG/kg body weight. Six days post injection, the mice were saline perfused and brains were immediately frozen on dry ice. 50 μm thick coronal cryosections were obtained and placed in an X-ray cassette along with 125I standards of known radioactivity. Positron-sensitive phosphor screens (MS, MultiSensitive, PerkinElmer, Downers grove, Ill., USA) were placed onto the samples for five days of exposure and then scanned at a resolution of 600 dots per inch in a Cyclone Plus Imager system (Perkin Elmer). The resulting digital images were normalized to the standards with ImageJ.

Antibody Treatment and Ex Vivo Analyses

Tg-ArcSwe mice, 14 months of age, were treated with a single injection of placebo (PBS), RmAb158-scFv8D3 (6.6 mg/kg body weight; 1.32 mg/ml in PBS) or RmAb158 (5.0 or 50 mg/kg body weight; 1 or 10 mg/ml in PBS). Radiolabeled protein of the same type as used for the treatment and equivalent to 0.05 mg/kg IgG, was mixed into the antibody solution. The specific activity was 71.2±7.6 MBq/nmol for [$^{125}$I]RmAb158-scFv8D3 and 71.9±3.6 MBq/nmol for [$^{125}$I]RmAb158. Mice were lightly sedated with isoflurane (Isoflurane Baxter®, Baxter Medical AB, Kista, Sweden), placed in a plastic holder and intravenously (i.v.) administered with 5 μl antibody solution/g body weight. Blood samples were taken from the tail at 1, 24, 48 h and a final blood sample was taken from the heart 72 h after injection, followed by saline perfusion and isolation of the brain. Radioactivity was measured in brain and plasma with a γ-counter (1480 Wizard™, Wallac Oy, Turku, Finland) and the antibody concentration in plasma and brain, quantified as % of the injected dose (ID) per g tissue, were calculated as set out in Example 2.

ELISA Analyses of Aβ Pathology

Brain concentrations of soluble and total Aβ were measured as described previously Syvanen, S., et al. (Neuroimage 148: 55-63 (2017)). In short, brain tissue was homogenized at a 1:5 weight:volume ratio in TBS with complete protease inhibitors (Roche; Sigma Aldrich, Stockholm, Sweden), then mixed 1:1 with TBS and centrifuged for 1 h at 100 000×g. For total Aβ, the original TBS extract was mixed with concentrated formic acid to a concentration of 70%, followed by homogenization as above and centrifugation at 16 000×g. Aβ oligomers and protofibrils were measured with a homogenous ELISA using 82E1 (IBL International/Tecan Trading AG, Switzerland) as both capture and detection antibody. 82E1 is specific to the N-terminal Aβ neoepitope generated after β-secretase cleavage of AβPP. A 96-well half-area plate was coated overnight with 12.5 ng per well of 82E1, then blocked with 1% BSA in PBS. TBS extracts were diluted 1:10 and incubated overnight at +4° C., followed by detection with biotinylated 82E1 (0.25 μg/ml), SA-HRP (1:2000, Mabtech AB) and K blue aqueous TMB substrate (Neogen Corp., Lexington, Ky., USA). For Aβ1-40 and Aβ1-42, 96-well plates were coated overnight with 100 ng per well of polyclonal rabbit anti-Aβ40 or anti-Aβ42 (Agrisera, Umeå, Sweden) and blocked with 1% BSA in PBS. Formic acid extracts were neutralized with 2M Tris and diluted 10 000× (Aβ1-40) or 2 000× (Aβ1-42) and incubated overnight at +4° C. After incubation with biotinylated 82E1 (0.25 μg/ml) signals were developed and read as above. All dilutions were made in ELISA incubation buffer.

Immunohistochemistry

Aβ pathology was visualized with Aβ40 immunostaining as previously described (Magnusson K. et al, supra) on 50 μm thick croysections adjacent to sections used for ex vivo autoradiography. Sections were fixed in 4% PFA in PBS for 20 min at room temperature, washed in PBS and then incubated 40 min in pre-heated citrate buffer (25 mM, pH 7.3, 100° C. at the start of the procedure) for antigen retrieval. Sections were then transferred to 70% formic acid for 5 min at room temperature and washed under a constant flow of fresh MQ-H2O for another 5 min. Endogenous peroxidase activity was blocked with DAKO peroxidase block (Agilent Technologies, Kista, Sweden) during 15 min and permeabilized in 0.4% triton in PBS for 5 min. After 10 min in DAKO-block (0.25% casein in PBS) to inhibit unspecific binding, sections were incubated overnight with 0.5 μg/ml polyclonal anti-Aβ40 antibody (Agrisera, Umea, Sweden), followed by a 30 min incubation with 5 μg/ml biotinylated goat anti-rat (Vector Laboratories Inc., Burlingame, Calif.) and 30 min with Streptavidin-HRP (Mabtech AB). The staining was developed with NOVA RED chromogen (Vector Laboratories Inc.) for 10 min on a shaker and then washed in MQ-H2O for 1 min and quickly dipped first in 95% EtOH and then 99.9% EtOH. Sections were air-dried, mounted with DPX mounting medium (Sigma Aldrich, Sweden) and analyzed with Nikon microscope (DXM1200F, Nikon Instruments Inc., Melville N.Y., USA).

Statistical Analyses

Results are presented as mean±standard deviation. Data was analyzed with one-way analysis of variance (ANOVA) followed by Bonferroni's post hoc test. Statistical analyses as well as plasma curve fit (one phase decay) and area under the curve were calculated with GraphPad Prism 5.0 (GraphPad Software, Inc, La Jolla, Calif., USA).

Results

Figure 9:
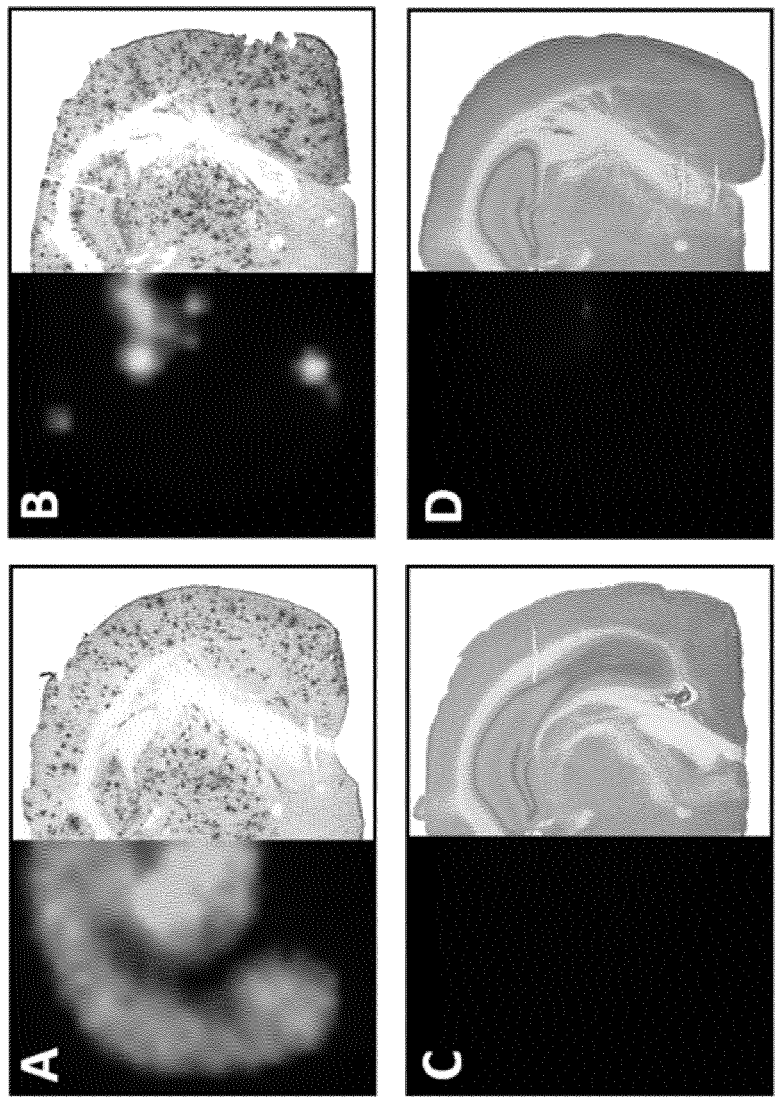
FIG. 9A-D are images showing global distribution of antibody in the brains of 18 month old tg-ArcSwe mice injected with [$^{125}$I]RmAb158-scFv8D3 (A) and [$^{125}$I]RmAb158 (B), six days post injection, visualized with ex vivo autoradiography (left) in comparison with Aβ40 immunostaining (right). While [$^{125}$I]RmAb158-scFv8D3 was distributed throughout the whole brain, [$^{125}$I]RmAb158 concentrated to central parts of the brain. For comparison, wt animals were also injected with [$^{125}$I]RmAb158-scFv8D3 resulting in no signal (C) and [$^{125}$I]RmAb158, where a faint signal was detected centrally in the brain (D).

To assess antibody distribution within the brain tissue, wildtype (wt) as well as 18 months old tg-ArcSwe mice with abundant Aβ pathology were injected with RmAb158-scFv8D3 and RmAb158 labeled with iodine-125 ($^{125}$I). Mice were saline perfused six days post injection and their brains were coronally sectioned for ex vivo autoradiography and Aβ40 immunostaining. As displayed in FIG. 9, the global distribution of the antibodies in the brain parenchyma was fundamentally different. The bispecific [$^{125}$I]RmAb158-scFv8D3 was distributed throughout the whole brain and retained in brain areas with abundant Aβ pathology, as visualized by Aβ40 immunostaining of an adjacent section. In contrast, [$^{125}$I]RmAb158 was almost completely concentrated to central parts of the brain. The retention of both antibodies was specific to Aβ pathology since almost no signal was detected in wt mice.

Figure 10:
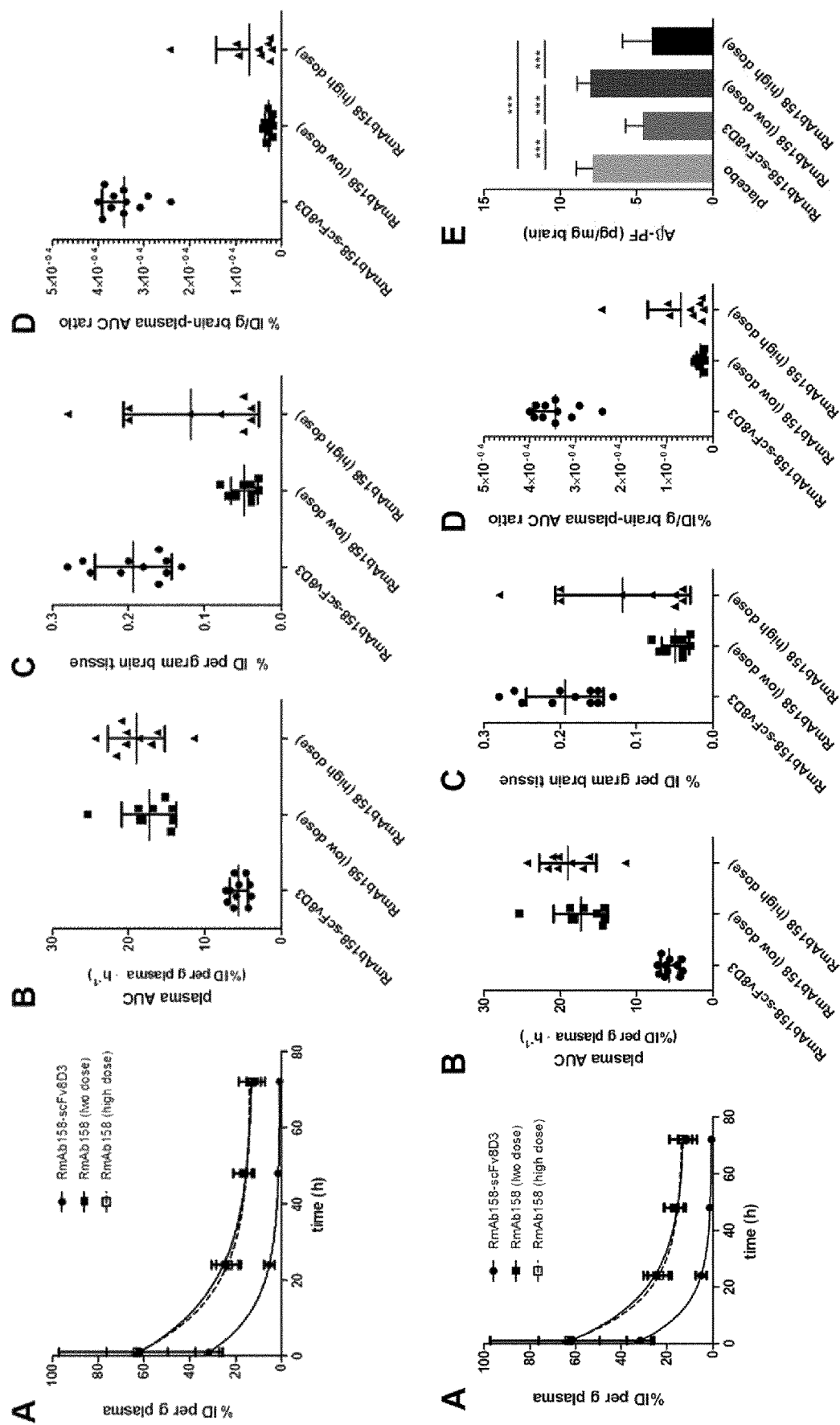
FIG. 10A-D are diagrams displaying: A. plasma pharmacokinetics of RmAb158-scFv8D3 and RmAb158 at two different doses during 72 h, expressed as % of the injected dose per g plasma. B. Drug exposure calculated from the area under the plasma curve in (A). C. Brain retention of antibodies expressed as % of the injected dose/gram brain tissue 72 h post injection. D. A ratio of the antibodies' brain retention to drug exposure 72 h post injection, to display their relative efficiency to enter and be retained in the brain.

Next, to study the impact of the improved brain distribution on the antibodies' ability to reduce brain levels of soluble Aβ protofibrils, a short term immunotherapy study was conducted in 14 month-old tg-ArcSwe mice. Divided in four groups of 10-11 individuals, the mice were given a single intravenous injection of: PBS (placebo); low dose of RmAb158-scFv8D3 (6.6 mg/kg body weight, equal to 5 mg/kg IgG); low dose of RmAb158 (5 mg/kg body weight) or high dose of RmAb158 (50 mg/kg body weight). All antibody doses were supplemented with trace amounts of $^{125}$I-labeled antibody of the same type to track concentrations in blood and brain. The bispecific antibody displayed a shorter half-life in blood compared with unmodified RmAb158 (FIG. 10A), resulting in almost four-fold lower drug exposure, as demonstrated by the area under the curve, displayed in FIG. 10B. The lower exposure also explains why a smaller difference in brain retention of the antibodies at three days (FIG. 10C) was observed as compared to the previously observed ten-fold difference at 2 h post injection. However, when adjusted for the reduced exposure, we still found a ten-fold more efficient transport into the brain (FIG. 10D).

Following saline perfusion, the brains of the antibody treated mice were isolated. The right hemisphere was fixed and paraffin embedded for imunohistochemical analyses whereas the left hemisphere was homogenized in TBS and formic acid (FA) to obtain extracts of soluble and total Aβ respectively. Using a homogenous ELISA with Aβ N-terminal specific 82E1 as both capture and detection antibody (Xia, W., et al., Arch Neurol 66(2):190-199 (2009)), it was found that brain levels of soluble Aβ oligomers and protofibrils were decreased by more than 40% in the group of mice treated with the bispecific RmAb158-scFv8D3 (FIG. 10E) in comparison with placebo. In contrast, an equimolar dose of RmAb158 had no effect on the levels of soluble Aβ aggregates, whereas the ten-fold higher dose displayed a similar reduction as the bispecific antibody. As expected from a single injection treatment paradigm, none of the treatment groups displayed any significant effect on levels of total Aβ, as measured with Aβ1-40 and Aβ1-42 ELISA in FA soluble brain extracts (data not shown).

Example 4: Generation and Characterization of a Recombinant Bispecific Alpha-Synuclein-TfR Antibody Cloning, Expression and Purification of RmAb48-scFv8D3

Cloning, expression and purification of a recombinant bispecific alfasynuklein-TfR antibody RmAb48-scFv8D3 was carried out essentially as set out in Example 1. MAb48 is disclosed in WO 2011/104696 and denoted "48B11/8" and decribed inter alia on pages 31-32 in Tables 1 and 2.

Results

A recombinant bispecific alfasynuklein-TfR antibody was successfully produced and characterized in accordance with Example 1. A single chain variable fragment (scFv), comprising the heavy and light chain variable regions of 8D3 connected to each other by a linker, was attached to the C-terminus of each of the RmAb48 light chains via a short peptide linker. The resulting protein thus had a conformation in accordance with the protein conformation shown in FIG. 1A.

Example 5: In Vivo Studies of Brain Distribution and Peripheral Biodistribution with Radiolabeled RmAb48-scFv8D3

The methods and materials used in this study were essentially the same as the methods and materials set out in Example 2.

Animals

Wild-type C57bl6 animals (wt), both males and females were used for studies of brain distribution of RmAb48-scFv8D3. The animals were housed and fed as described in Example 2.

Radiochemistry

Alpha-synuclein binding antibody RmAb48 and bispecific RmAb48-scFv8D3 was labelled with iodine-125 ($^{125}$I) using direct radioiodination (Greenwood, F. C. et al, Biochem. J. 89,114-123 (1963)). Labelling was carried out essentially as set out in Example 2.

Ex Vivo Studies

Mice were intravenously (i.v.) injected with 0.89±0.06 MBq [$^{125}$I]RmAb48 (n=3) or 0.92±0.02 MBq [$^{125}$I]RmAb48-scFv8D3 (n=3), which equals a dose of 0.05 mg/kg. After perfusion, the brain was isolated and the cerebellum was separated from the rest of the brain before the brain tissue samples were frozen on dry ice. Radioactivity in blood, brain and cerebellum was measured with a γ-counter (1480 Wizard™, Wallac Oy, Turku, Finland). The brain, cerebellum and blood concentrations, as well as the tissue-to-blood ($K_p$) concentration ratio, were calculated as described in Example 2.

Results

RmAb48-scFv8D3 and RmAb48 were radiolabeled with $I^{125}$ in yields around 70% for in vivo studies in mice.

To test the ability of the scFv8D3 moiety to enable TfR mediated transcytosis in vivo, wt mice were administered with [$^{125}$I]RmAb48 or [$^{125}$I]RmAb48-scFv8D3 and the brains were isolated 2 h after injections. The brain concentrations, expressed as percent of injected dose per gram brain tissue (% ID/g, Equation 1) was 0.04±0.01 and 1.04±0.26 for [$^{125}$I]RmAb48 and [$^{125}$I]RmAb48-scFv8D3, respectively. Thus, the scFv8D3 modification lead to an 25-fold increase in brain concentrations at this time point. The brain-to-blood concentration ratio (Kp, see equation above) was 0.0020±0.0004 and 0.089±0.015 for the two ligands, respectively. Hence the Kp, which takes into account available ligand in blood, was increased 54-fold by the scFv8D3 modification of RmAb48.

The invention claimed is:

1. A brain delivery protein, comprising a target binding antibody which binds to a target in a mammalian brain; two carrier moieties, each of which being capable of monovalent interaction with a protein expressed on a blood brain barrier (BBB) endothelial cell, wherein said interaction between the carrier moiety and the protein expressed on a BBB endothelial cell takes place through one single epitope, wherein each of said carrier moieties is linked to a C-terminal end of a light chain of the target binding antibody by a linker, wherein each of said linkers individually consist of a peptide having an amino acid sequence consisting of 5-15 amino acid residues, thereby enabling monovalent interaction of said brain delivery protein with said protein expressed on a BBB endothelial cell.

2. The brain delivery protein according to claim 1, wherein said linker has one or more of the following characteristics:
   (i) it is a glycine rich linker;
   (ii) it is a hydrophilic linker;
   (iii) it comprises amino acid residues having small side chains, and/or
   (iv) it comprises a peptide comprising at least one proline residue.

3. The brain delivery protein according to claim 1, wherein each of said carrier moieties is linked to the target binding antibody by a linker, said linker comprising a peptide having the amino acid sequence as set out in SEQ ID NO:1.

4. The brain delivery protein according to claim 1, wherein each of said carrier moieties comprises an antibody fragment selected from a scFv, Fv, scFab, or a $V_{HH}$; transferrin or a variant thereof, or a variant of protein Z derived from domain B of staphylococcal protein A.

5. The brain delivery protein according to claim 4, wherein each of said carrier moieties comprises a scFv.

6. The brain delivery protein according to claim 1, wherein said protein expressed on a BBB endothelial cell is selected from transferrin receptor (TfR), insulin receptor (InsR), insulin-like growth factor receptor, low density lipoprotein receptor-related protein 8 (Lrp8), low density lipoprotein receptor-related protein 1 (Lrp1), CD98, transmembrane protein 50A (TMEM50A), glucose transporter 1 (Glut1), basigin (BSG) and heparin-binding epidermal growth factor-like growth factor.

7. The brain delivery protein according to claim 6, wherein said protein expressed on a BBB endothelial cell is TfR.

8. The brain delivery protein according to claim 1, wherein said target binding antibody is a full length antibody, Fab, a F(ab')$_2$ or a Fv.

9. The brain delivery protein according to claim 8, wherein said target binding antibody is a full length antibody.

10. The brain delivery protein according to claim 1, wherein said target in the brain is selected from amyloid β (Aβ) peptide, alpha synuclein, superoxide dismutase (SOD), huntingtin, transthyretine, β-secretase 1, epidermal growth factor, epidermal growth factor receptor 2, Tau, phosphorylated Tau, apolipoprotein E4, CD20, prion protein, leucine rich repeat kinase 2, parkin, presenilin 2, gamma secretase, death receptor 6, amyloid precursor protein, p75 neurotrophin receptor, neuregulin and caspase 6.

11. The brain delivery protein according to claim 10, wherein said brain target is an Aβ peptide.

12. The brain delivery protein according to claim 11, said protein comprising an Aβ binding antibody, and two carrier moieties being fragments of anti-TfR antibodies.

13. The brain delivery protein according to claim 12, wherein said Aβ binding antibody is mAb158/BAN2401 and each of said carrier moieties is a scFv8D3, wherein each of said scFv8D3 is linked to a C-terminal end of a light chain of said mAb158/BAN2401, said protein further comprising two linkers, each linker having an amino acid sequence as set out in SEQ ID NO:1, for linking said scFv8D3 to said mAb158/BAN2401.

14. The brain delivery protein according to claim 11, wherein said brain target is a soluble Aβ aggregate.

15. The brain delivery protein according to claim 14, wherein said soluble Aβ aggregate is an oligomer or protofibril.

16. The brain delivery protein according to claim 10, wherein said brain target is alpha synuclein, preferably soluble alpha synuclein, such as soluble alpha synuclein selected from oligomers and protofibrils.

17. The brain delivery protein according to claim 16, comprising an alpha synuclein binding antibody, and two carrier moieties being fragments of anti-TfR antibodies.

18. The brain delivery protein according to claim 17, wherein said alpha synuclein binding antibody binds human alpha synuclein protofibrils, preferably said alpha synuclein binding antibody does not bind alpha synuclein monomers.

19. The brain delivery protein according to claim 17, wherein said alpha synuclein binding antibody is mAb48 and each of said carrier moieties is a scFv8D3, wherein each of said scFv8D3 is linked to a C-terminal end of a light chain of said mAb48, said protein optionally further comprising two linkers, each linker having an amino acid sequence as set out in SEQ ID NO:1, for linking said scFv8D3 to said mAb48.

20. The brain delivery protein according to claim 1, said protein being a fusion protein.

21. A method for treatment of a brain disorder in a mammal, wherein said brain disorder is a neurodegenerative disorder selected from the group consisting of Alzheimer's disease, Lewy body dementia (LBD), Amyotrophic lateral sclerosis (ALS), Frontotemporal dementia, tauopathies, Parkinson's disease dementia (PDD); multiple system atrophy; Creutzfeldt-Jakob disease and Huntington's disease, comprising administering to said mammal a therapeutically effective amount of a brain delivery protein according to claim 1.

22. The method according to claim 21 wherein said neurodegenerative disorder is Alzheimer's disease.

23. The method according to claim 22 wherein the antibody is mAb158/BAN2401 and wherein said antibody binds an Aβ peptide.

24. The method according to claim 21 wherein said neurodegenerative disorder is Parkinson's disease dementia.

25. The method according to claim 24 wherein said antibody is mAb48 and wherein said antibody binds alpha synuclein.

26. A method for diagnosing and/or detecting a brain disorder in a mammal suspected of having, or being at risk of developing said disorder, comprising administering to said mammal a brain delivery protein according to claim 1, wherein said brain disorder is a neurodegenerative disorder selected from the group consisting of Alzheimer's disease, Lewy body dementia (LBD), Amyotrophic lateral sclerosis (ALS), Frontotemporal dementia, tauopathies, Parkinson's disease dementia (PDD); multiple system atrophy; Creutzfeldt-Jakob disease and Huntington's disease, wherein said brain delivery protein comprises a label enabling detection of said target in the brain, wherein said protein is administrated in an amount sufficient to enable diagnosis and/or detection of said target in the brain, and detecting said target in the brain.

27. The method according to claim 26, wherein said label is selected from a radiolabel, a fluorophore, a chromophore, and an affinity tag.

* * * * *

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: Linker

<400> SEQUENCE: 1

Ala Pro Gly Ser Tyr Thr Gly Ser Ala Pro Gly
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Linker

<400> SEQUENCE: 2

Gly Ser Thr Ser Gly Gly Gly Ser Gly Gly Gly Ser Gly Gly Gly
1               5                   10                  15

Ser Ser
```